United States Patent [19]

Picciolo et al.

[11] Patent Number: 4,777,133
[45] Date of Patent: * Oct. 11, 1988

[54] DEVICE FOR QUANTITATIVE ENDPOINT DETERMINATION IN IMMUNOFLUORESCENCE USING MICROFLUOROPHOTOMETRY

[75] Inventors: Grace L. Picciolo, Rockville, Md.; David S. Kaplan, Fairfax, Va.

[73] Assignee: The United States of America as represented by the Secretary of the Department of Health and Human Services, Washington, D.C.

[*] Notice: The portion of the term of this patent subsequent to Nov. 12, 2003 has been disclaimed.

[21] Appl. No.: 801,965

[22] Filed: Nov. 26, 1985

Related U.S. Application Data

[63] Continuation-in-part of Ser. No. 619,325, Jun. 11, 1984, Pat. No. 4,622,291.

[51] Int. Cl.$^4$ .................... C12Q 1/02; G01N 33/571; G01N 35/00; G01N 33/552
[52] U.S. Cl. .................... 435/29; 250/252.1; 424/3; 424/7.1; 435/34; 436/46; 436/511; 436/527; 436/531; 436/537; 436/800; 436/807; 436/826
[58] Field of Search .................. 424/3, 7.1; 435/7, 29, 435/4, 34, ; 436/825, 176, 510, 511, 527, 531, 537, 800, 807, 826; 250/252.1

[56] References Cited

U.S. PATENT DOCUMENTS

| | | | |
|---|---|---|---|
| 4,544,546 | 10/1985 | Wang et al. | 424/3 |
| 4,576,912 | 3/1986 | Yaverbaum et al. | 435/7 |
| 4,582,791 | 4/1986 | Khanna et al. | 435/7 |
| 4,612,281 | 9/1986 | Desmonts et al. | 435/7 |
| 4,622,291 | 11/1986 | Picciolo et al. | 424/3 |

OTHER PUBLICATIONS

Kaplan et al., American Society for Microbiology, 1981, C 130.
Kaplan et al., 82nd Meeting of the American Society for Microbiology, 1982, p. 1.
Picciolo et al., Defined Immunofluorescence, Immunoenzyme Studies and Related Labeling Tech., 1982.
Kaplan et al., Defined Immunofluorescence, Immunoenzyme Studies and Related Labeling Tech., 1982.
Picciolo et al., Automation of Diagnostic Cytology, 1983, Art. 62.
Picciolo et al., Fourth International Congress of Automation in Cytology, Jun. 1983.
Kaplan et al., American Society for Microbiology, 1983, Q 27.

Primary Examiner—Robert J. Warden
Assistant Examiner—Florina B. Hoffer
Attorney, Agent, or Firm—Holman & Stern

[57] ABSTRACT

The present invention discloses a device and a process for quantitation of *Toxoplasma gondii* and *Treponema pallidum* antibody titer in a biological sample by immunofluorescent photometric microscopy. The process comprises:

(a) reacting a specimen of said sample with an immunofluorescent reagent in a mounting medium containing a protective agent in an amount sufficient to reduce fading of a fluorescent reaction product less than 25% of initial fluorescent intensity;
(b) localizing the specimen under transmitted, visible light;
(c) reducing the effect of counterstain intensity by filters in emission light path;
(d) measuring the sample using a fast shutter;
(e) calibrating the photometer used in said microscopy by a stable fluorophore;
(f) recording intensity of fluorescence of said specimen compared to standard negative and positive controls;
(g) reducing effect of polar staining by substracting the corrected intensity of corresponding dilution of the negative control from the sample reading;
and (h) assigning a numerical endpoint for serum antibody levels against *Toxoplasma gondii* or *Treponema pallidum*.

5 Claims, 16 Drawing Sheets

DEVICE FOR QUANTITATIVE ENDPOINT DETERMINATION IN IMMUNOFLUORESCENCE USING MICROFLUOROPHOTOMETRY

The present application is a continuation-in-part of the application Ser. No. 619,325 filed June 11, 1984 now U.S. Pat. No. 4,622,291.

BACKGROUND OF THE INVENTION

1. Technical Field

The present invention is related to a method and device for quantitative determination of fluorescent reaction product endpoint in immunofluorescence using microfluorophotometry. More particularly, the present invention is related to standardization of various parameters, calibration of components or devices and determination of reaction conditions for a reliable, stable and reproducible quantitation of fluorescent reaction product in immunofluorescent microscopy or microfluorophotometry.

2. Prior Art

Current method for immunofluorescent (IF) test involves a subjective evaluation of the end point (titer) which is dependent, inter alia, upon the observer's expertise, experience and judgment. This subjectivity is further complicated by the rapid fading of the fluorescent reaction product (FRP) under the test conditions routinely employed. Thus, as the art is presently known, the outcome of an IF test becomes a function of time and judgment. In fact, there being no better or objective method for IF assay, researchers have generally conceded that rapid fading of fluorophores would have to be tolerated if IF is opted as the procedure of choice. Nairn et al., *Clin. Exp. Immunol.* 4, 697–705 (1969); Johnson et al., *J. Immunol. Meth.* 55, 231–242 (1982); Schauenstein et al., *J. Immunol. Meth.* 8, 9–16 (1975); Wick et al., *Ann. New York Acad. Sci.* 254, 172–174 (1975); McKay et al., *Immunology* 43, 591–602 (1981).

Various techniques have been used to protect the sample from fading. These are summarized in Table 1.

TABLE 1
METHODS FOR THE REDUCTION OF FADING

| Technique | Investigator |
|---|---|
| (1) Localization under phase contrast | Ploem, Golden, Fukuda, Geyer |
| (2) Fast, epi-shutter excitation | Ploem, Golden, Geyer, Kaufmann Nairn |
| (3) Chemical Agents | Gill, Johnson, Sedat, Giloh, Kaplan, Picciolo |
| (4) Pre- or Post-illumination | Fukuda, Fujita |
| (5) Variable iris diaphragm on objective | Golden, Ploem |
| (6) Neutral density filters | Nairn, Ploem |
| (7) Light sources | Goldman, Haaijman, Johnson |
| (8) Excitor/barrier filters | Goldman, Haaijman, Nairn, McKay |
| (9) Field diaphragms | Golden, Ploem, Haaijman |

Of these, a more practical and feasible technique appears to be the use of chemical additives in the mounting medium to protect the fluorophore from the effects of the excitation light.

Protection from fading would make exposure of the specimen to the exciting light less critical. This would allow ease in the localization of the fluorescent specimens and permit more accurate discrimination between weakly positive and negative results, which is difficult if the sample is rapidly fading.

Certain tests, such as determination of the type of *Herpes* present, require finding any positive cells that may be present on the entire slide. This searching procedure may take several minutes and must be done during excitation to recognize the presence of the positives. If fading is rapid, positives may be missed. Protection from fading in these cases is critical.

Reducing the fading would also significantly improve quantitation of the FRP on the IF microscopy slides. Retarding fading would permit longer scan times on slides without concomitant decrease in fluorescence intensity. This would permit the use of automated or semi-automated instrumentation which could scan a slide and determine the endpoint quantitatively.

Rapidly fading specimens account for many false negatives in the clinical laboratory. In some cases, by the time the technician has set up the slide on the microscope, the weakly positive cell has faded to a negative cell. In the case of antinuclear antibody (ANA) positive cells, the technician cannot properly identify the staining pattern if the specimen is rapidly fading. Stabilization of the fluorescence emission is, therefore, necessary for objective and quantitative determination of antibody level.

A factor which must also be considered in the evaluation of the IF assay, is the variability due to the instrumentation.

Earlier methods used microcapillaries filled with the fluorophore of interest. In this method the microcapillary diameter is measured microinterferometrically, allowing exact calibration of the microscope fluorometer and correlation of the measured fluorescence intensities with the mass of the excited fluorochrome. Serntz, et al., *Fluorescence Techniques in Cell Biology* Springer-Verlag, N.Y., pp 41–49 (1973). Certain applications may not require an exact calibration, but an easier-to-perform secondary standardization may be satisfactory.

Recent work by Jensen et al., *J. Immuno. Meth.* 42: 343–353 (1981) used a particle of europium salt phosphor as a daily standard.

The Applicants have now improved the immunofluorescent methodologies by various means amongst which are: (a) removing the subjective evaluation of endpoint determination by providing a quantitative measure; (b) providing a reagent-reactivity-monitor which includes performance testing associated with a numerical value, (c) providing a calibration standard for inter-laboratory brightness comparison; and (d) achieving a quantitative measure by a fading retardant means.

SUMMARY OF THE INVENTION

It is, therefore, an object of the present invention to provide an agent to reduce fading of fluorescent reaction product in a microfluorophotometric test system.

It is another object of the present invention to provide a reproducibly stable system for quantitative determination of fluorescent reaction product in microfluorophotometry.

It is a further object of the present invention to provide a device and method for use in a photo-fluorescence system to measure microscopically observed epifluorescence intensity in terms of electromotive force.

It is yet another object of the present invention to provide a method using a computer-controlled microscope-photometer for measuring fluorescence intensity as a voltage output.

It is still another object of the present invention to provide calibrators for inter- and intra-laboratory comparison of fluorescence microphotometry.

These and other objects and advantages will become evident as the description of the invention proceeds.

BRIEF DESCRIPTION OF THE DRAWINGS

These and other objects, features and many of the attendant advantages of the invention will be better understood upon a reading of the following detailed description when considered in connection with the accompanying drawings wherein.

DETAILED DESCRIPTION OF THE INVENTION

Figure 1:
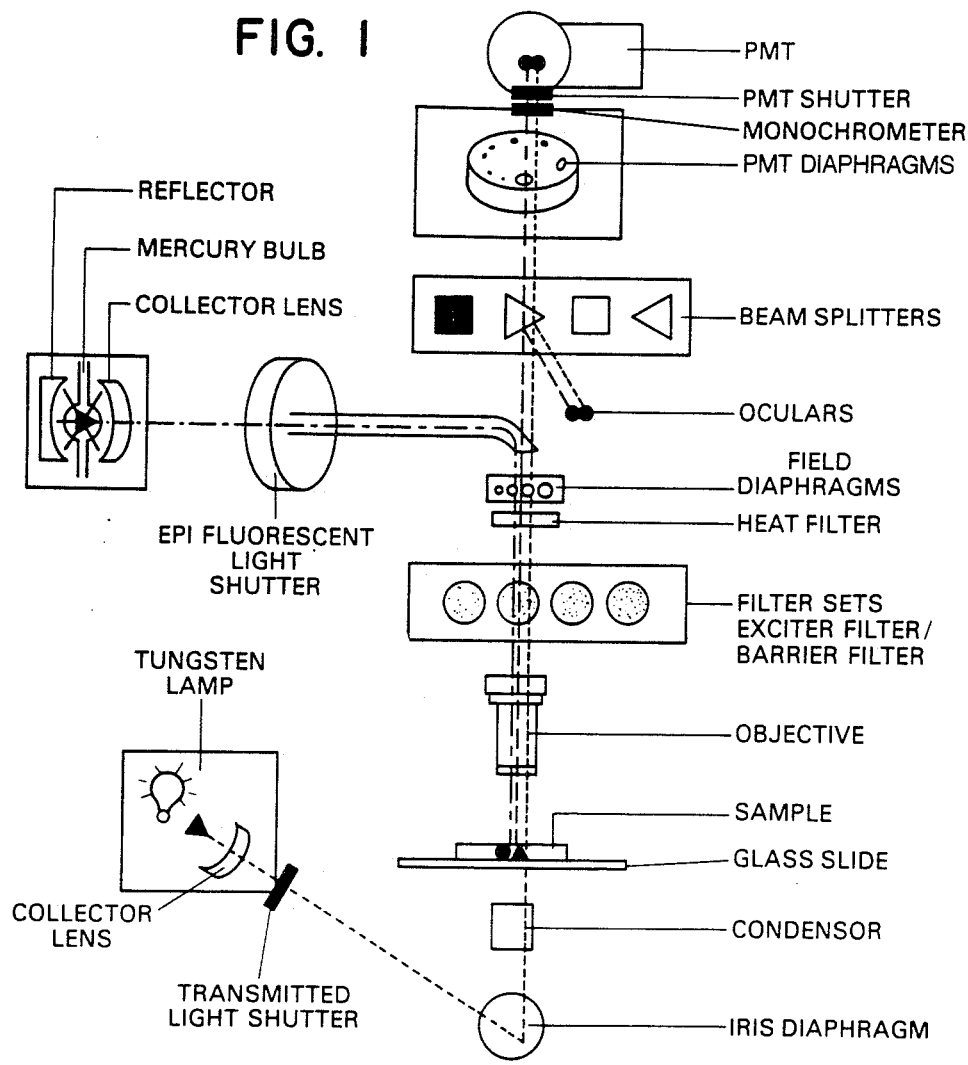
FIG. 1 is a schematic of light path for the Zonax microscope fluorophotometer wherein the epi-fluorescence exciting light (mixed) transmitted visible light (small dash) and the emission light (long dash) paths are shown.

Various objects and advantages as suggested herein are achieved by the present invention which includes a method for quantitative determination of fluorescent endpoint in a fluorescent reaction in microscopy comprising:

(a) incorporating a protective agent in a suitable mounting medium in an amount sufficient to reduce fading of fluorescent reaction product less than 25% of initial fluorescent intensity;

(b) calibrating photometer used in said microscopy with a stable emitter; and (c) recording the intensity of fluorescence of said fluorescent reaction product by means for measuring light intensity.

As used herein fading refers to the time-dependent decrease in fluorescence intensity upon continuous exposure to ultraviolet (UV) exciting light, as distinguished from quenching, which is a static reduction in the intensity due to some environmental or chemical condition present. Changes in the fluorescence intensity with time are a measure of the fading rate, while differences in the initial intensity under various environmental conditions are an evaluation of quenching.

A. Instrumentation

Any instrument suitable for use in fluorophotometry can be used. Two general classes of instrumentation which could be employed for intensity measurements of FRP are as follows.

I. Macrofluorophotometers

Macrofluorophotometers are designed to accept a cuvette that holds a volume of fluorescent solution or a solid sample holder which accommodates a flat plate. Both an excitation and an emission monochromator with variable slit widths are in the optical path (Sernetz and Thaer, *Fluorescence Techniques In Cell Biology*. New York: Springer-Verlag, pp 41–49, 1973). A corrected emission spectrum is obtained using a standard emittor as a wave length calibration. Macrofluorophotometers are effectively used for screening of the effects of the chemical environment on the fluorescence emission intensity, monitoring the purification procedures for the production of labeled conjugate and determination of the excitation and emission spectra of fluorophores. Detailed description of a Perkin-Elmer 650–40 spectrofluorophotomer and its use in predicting effectiveness of reducing agents to protect the FITC-labeled conjugates from fading is provided herein infra. Only part of the solution of the fluorophore in a cuvette in a macrofluorophotometer is exposed to the excitation beam. The rest of the molecules are free to diffuse and effectively replenish the faded molecules, particularly if the solution is being mixed. Therefore, confirmation of the effectiveness of fading protection must be made in the microfluorophotometers.

II. Microfluorophotometers

Various types of microscopes are available with epifluoroescence excitation and with a photometer to detect the emitted light intensity and convert it to a digital signal and any one system could be used. Some of such systems have been described by Ploem, Chap. 10: Quantitative Immunofluorescence, pp. 63–73, Blackwell Sci. Pub. (1970); J. Histochem. Cytochem. (22), 7, 668–677 (1974); Ann. New York Acad. Sci. Vol. 254, pp. 4–20 (1975); Chapter 6: Automated Methods in Immunofluorescence Studies, pp. 73–94 (1982); Taylor and Heimer, J. Biol. Standardization 2, 11–20 (1974); Thaer, Acad. Press, New York, Vol. 1 pp. 409–426 (1966); Golden and West, J. Histochem. Cytochem. 22(7), 495–505 (1974).

FIG. 1 shows a typical epi-fluorescence optical path whereby the exciting light is incident through the objective on the specimen and the fluorescence emission is collected by the same objective and then focused on the photocathode surface of the photomultiplier tube (PMT). An advantage of epi-illumination is a reduction of distortion of the emission spectrum due to reabsorption where there is an independence of section thickness. Therefore, one can measure surface fluorescence of opaque objects. There is also, more precise alignment due to simultaneous focusing since the objective is the condensor (Rigler, Acta Physiolog. Scandin. 67 (supplementum 267), pp. 117 (1966); Pearse and Rost, J. Microsc. 89(3), 321–328). Several microscope systems are commercially available with microprocessor control, including the operation of a 0.25 or 0.5 micron scanning stage. A preferred Zeiss Zonax system used herein is described infra.

B. Fluorescence Affecting Factors

In order to appreciate the invention, several factors which affect fluorescence intensity should be understood. These are summarized below.

I. Optical

Some of the optical components which can contribute to fading are as follows.

1. Lamp housing

Depending on the design of the housing for the excitation light source, the amount of light reflected to the collector lens will vary. Since the fading is dependent on the excitation energy, if the excitation light is scattered in the lamp housing and is lost through the baffles, this is equivalent to a decrease in excitation energy and will result in less fading and less signal. The better designed lamp housings reflect a high percentage of the excitation light on the collector lens. In addition, lamp housings vary in their efficiency of dissipating the heat from the light source. Heat build-up can cause instability of the light source, i.e. wandering of the arc or misfiring of the arc. An unstable light source causes fluctuation in the output from the lamp and will cause variations in the emission.

2. Light Source

There are a variety of light sources available for fluorescence excitation. Lasers offer the advantage of delivering monochromatic light and can generate pulses of light as short as 0.4 microseconds, Wick et al., Ann. New York Acad. Sci. 254, 172–174 (1975); Bergquist Scand. J. Immunol. 2, 37–44 (1973). These sources also give a high output of energy for exciting weakly fluorescent specimens. Additionally, lasers have a long lifetime compared to conventional light sources such as mercury, xenon or halogen lamps. Mercury arc lamps emit strongly at several lines in the UV and blue light regions (365 nm, 405 nm and 435 nm). Even though there is no special line in the spectral range of fluorescein isothiocyanate (FITC) absorption (440–490 nm), these sources are good for FITC emission (Goldman, Acad. Press, N.Y. (1968); Haaijman Inst. Experim. Gerontol. (1977). Xenon bulbs produce a continuous emission throughout the entire spectrum but the brightness per unit area is lower than with mercury bulbs (Goldman, Acad. Press, N.Y. (1968). In addition, xenon lamps require the use of more restrictive filters than with mercury bulbs, since the excitation light continues into the emission region of the dye (due to the continuous spectrum). Xenon and mercury bulbs cause considerable fading of the specimen. Halogen lamps do not emit as much blue light and emit lower intensities than mercury lamps. Therefore, halogen lamps, in general, are not suitable for fluorescence quantitation (Goldman, Acad. Press, N.Y. (1968). These lamps are useful when the specimen is brightly stained and the observer wants to eliminate fading as much as possible. Recently, the HBO 100 W mercury lamps have been developed with more stable arcs, more excitation energy and less heat output energy. They are operated with a stabilized power supply and are preferable.

3. Excitation Energy

Ploem, Ann. New York Acad. Sci. 177, 414–429 (1971) has shown that the fading rate is dependent on the excitation energy. Most researchers who perform experiments to measure fading have not measured the excitation energy of the light source, because the instrumentation is specialized and expensive. The output varies from day to day and decreases as the bulb ages. Factors such as type of light source, age of bulb, position of the collector lens, diffusion of the light beam over the specimen, type of heat filters, magnification and numerical aperture (NA) of the objective and the excitation filters all affect the excitation energy. It is clear, therefore, that the fading of the fluorescently stained specimens reported in the literature cannot be compared unless related to the power density of the excitation light source.

4. Collector lens

As the light exits the lamp housing, the collector lens concentrates or diffuses the light. The excitation energy is dependent on the position of the collector lens. If the collector lens is adjusted so that the light is focused on a small spot on the specimen, then the energy per unit area will be higher than if the light is diffused over the entire field. Therefore, if the light is concentrated rather than diffused in order to increase the emission intensity, there will be increased fading of the specimen.

5. Heat Filters

Heat filters are placed in the light path to filter out the infra-red radiation so that the excitation filters are not cracked by the constant, intense radiation from the light source. In addition, these filters will decrease the transmission of light in the UV region to varying degrees, depending on the type and quality of the filter. Goldman, *Acad. Press, New York* (1968).

6. Excitation and Neutral Density Filters

The amount and wavelength of the exciting light reaching the specimen is dependent on the filters used. Broad-band excitor filters allow wider wavelength band to reach the specimen with more fading than narrow-band excitor filters. McKay et al., *Immunology* 43, 5910602 (1981) showed that using narrow band FITC filters for blue light instead of UV+blue, reduced the fading and fluorescence intensity by equal amounts. Herzog et al., *J. Immunol. Meth.* 3, 211-220 (1973) also found that the rate of fading is dependent on the filters used. Schauenstein et al., "Immunofluorescence and Related Staining Techniques" pp. 81-95 (1978) compared the excitation spectra of free FITC and conjugated FITC. They found that conjugation of protein to the FITC molecule quenches the UV maxima at 280 and 340 nm (the UV region) as compared to free FITC. Since there is no quenching at the 496 peak (the blue region), blue excitation is preferrable when high intensities are desired. Ploem, *Ann. New York Acad. Sci.* 177, 414-429 (1971) compared the fading of antinucler antibody (ANA) positive cells stained with FITC using various excitation filter combinations. The first combination (GG 475 and two KP 490 filters) which has a high transmittance (about 80%) showed a very rapid loss of intensity within 0.25 second. The second filter combination (the first with a 25% transmittance neutral density filter added) showed a much slower decay of the fluorescence intensity. Enerback and Johansson, *Histochem. J.* 5, 351-362 (1973) showed that inserting graded neutral density filters into the exciting light path proportionally reduced the fading. Dichroic mirrors are interference dividing plates that reflect light of certain wavelengths through the objective and allow light of shorter or longer wavelengths to pass through the filter, being lost through scattering, Ploem Chapter 10: Quantitative Immunofluorescence, pp. 63-73 (1970). The fading could be significantly enhanced or reduced depending on how selectively the dichroic mirrors are filtering out the light.

7. Objectives

Since in epi-fluorescence, the objective acts as a condensor, the intensity of the light is dependent on the numerical aperture (NA) of the objective; the intensity increases as the square of the NA (Goldman, *Acad. Press, New York* (1968); Haaijman, *Inst. Experim. Gerontol.* (1977). The NA is defined as the product of the refractive index of the medium in which the aperture angle is measured and the sine of the aperture angle, Piller *Springer-Verlag, New York* (1977). A typical NA for low power objective is 0.65 and 1.25 for high power objective. Some objectives have a variable iris diaphragm which allows the control of the excitation of the specimen. While reducing the excitation (via this method) does reduce fading, it does not allow absolute quantitation of the emitted intensity. Unless there is a very specific way of assuring that the iris diaphragm is set to exactly the same place each time, one cannot absoutely compare the intensities of samples. The type of objective will also influence the fading. If the objective is made of several lenses which have been cemented together, there is approximately a 4% light loss each time the light passes through an air-glass interface, *Zeiss* (1960). Depending on the number of lenses in the objective, this light loss could be significant if one is attempting to quantitate the fluorescence intensity. It should be noted that a similar light loss is observed in excitation filters which are composed of several filters cemented together.

II. Excitation Time

Not only is fading dependent on the optical factors but also on excitation energy and the time and period of exposure. The longer a fluorescently-tagged specimen is exposed to the exciting light, the more the fading will occur, down to a minimal plateau level. Interspersing excitation with dark periods has an effect on the fading in some cases. This may result in recovery of some of the intensity and is variable with fluorophore, exposure and dark times, and excitation energy.

III. Environmental

In addition to the fading caused by the optical elements and excitation time, there are environmental factors which may affect fading. Haaijman *Inst. Experim. Gerontol.* (1977) compared the fading of aminoethyl-Sephadex bound FITC and Sepharose-bound FITC for 2 min under continuous excitation. FITC coupled to Sepharose faded 20% more than FITC coupled to aminoethyl Sephadex beads. It is concluded that fading is dependent on the matrix to which FITC is bound.

Haaijman, supra, tested the influence of pH on the fading in the presence or absence of protein (i.e. CNBr activated 4B-Sepharose-OVA-FITC vs 4B-Sepharose-FITC) to test the hypothesis that electrophilic groups near the FITC moiety influence the fading. Since the fading in the presence or absence of protein was similar at various pH levels, it was concluded that fading is not influenced by electrophilic centers in the protein to which it is coupled, but is a property of the molecule itself. McKay et al., *Immunology* 43, 591-602 (1981) found that when the pH of the buffered blycerol mounting medium was raised from 7.2 to 8.8, there was a 23% increase in the fluorescence intensity, but the rate of fading did not change.

Comparison of Fading

Since several factors, as enumerated above, affect the intensity of the emitted light, a comparative study of fading performed in various optical set-ups in different laboratories is difficult to make. No set fading parameters have been established to allow this comparison. Therefore, the fading percentages obtained at different times from various investigators are not necessarily comparable. However, an appreciation of the relative effectiveness of various conditions can be obtained from the following description.

A. Excitation Source

1. Laser

Several authors have used lasers to measure the fading of FITC-labeled conjugates (Wick et al., *Ann. New York Acad. Sci.* 254, 172-174 (1975); Kaufman et al., *J. Histochem. Cytochem.* 19, 469 (1971); Bergquist, *Scand. J. Immunol.* 2, 374-44 (1973); Bergquist et al., *Ann. New York Acad. Sci.* 254, 157-162 (1975); Schauenstein et al., *J. Histochem. Cytochem.* 28(9), 1029-1031 (1980). These investigators have compared the fading of the conjugate when the sample was excited by repeated, short pulses of light with a laser to the fading when the sample was exposed to a conventional light source such as a mercury or xenon arc lamp. Additionally, lasers have been used to measure recovery (percentage of the initial fluorescence intensity that is regained as the cells are left in a dark environment) following various periods of fluorescence excitation. Experiments combining fading and recovery have been useful in explaining the mechanism of fluorescence fading.

a. Argon-ion. laser

Kaufman et al., *J. Histochem. Cytochem.* 19, 469 (1971) measured the fading of FITC-labeled *Escherichia coli* cells using an Argon-ion laser source. They found that when using an Argon laser at a power density of 160 watts/cm$^2$, 89% of the initial *E. coli* intensity had faded within 10 seconds, under continuous irradiation. But, when the excitation time was reduced to milliseconds, no significant fading could be detected. Schauenstein et al., *Immunofluorescenct Technology*, pp. 27–36 (1982) found that free FITC in solution lost 40% of its initial intensity during the first 100 milliseconds of excitation with an Argon laser.

b. Pulsed dye laser

Bergquist and Nilsson, *Ann. New York Acad. Sci.* 254, 157–162 (1975) compared the fading of FITC-labeled glutaraldehyde-polymerized microspheres of purified human IgG excited with an HBO 200 W mercury lamp to the fading when the spheres were excited with a Chromabeam 1070 pulsed dye laser. The laser was adjsted to produce light of 495 nm. Bergquist, *Scand. J. Immunol.* 2, 37–44 (1973) has previously shown that when the spheres were exposed to a total of 125 pules (each pulse is 0.4 μs for a total exposure of 50 μs) and the resultant image was exposed to photographic emulsion, there were no signs of significant fading. In a second study (Bergquist and Nilsson, *Ann. New York Acad. Sci.* 254, 157–162 (1975), they repeated the previous study and quantitatively measured the fading by monitoring the deflections on an oscilloscope from the photomultiplier tube (PMT). They found that even after 50 laser pulses had illuminated an individual sphere, no fading was observed. However, after one second of exposure to a HBO 200 W mercury light, only 85% of the initial intensity remained.

c. Recovery

Since researchers and lab technicians are usually interested in observing a fluorescently stained field more than once (i.e. in the histopathological diagnosis of cancer cells or when observing the staining pattern in immunofluorescence diagnostic test kits), researchers are interested in determining the extent of permanent lowering of the intensity by prior excitation conditions. Maintaining the level of the initial intensity is important in the diagnosis of disease states since it is often necessary to have a second technicial or a physician review the test results. If the fluorescent field was irreversibly faded during the initial observation, then it is not possible to confirm the first technician's diagnosis and false positive or false negative results may be reported. Kaufman et al., *J. Histochem Cytochem.* 19, 469 (1971); Wick et al., *Ann New York Acad. Sci.* 254, 172–174 (1975) and Schauenstein et al., *J. Immunol. Meth.* 8, 9–16 (1975) found that recovery is dependent on the time of exposure to the excitation light source and the length of time the specimen is left in the dark following excitation. These authors found that minimum dark period of two seconds between laser pulses is necessary to get recovery of the fluorescence. Schauenstein et al., "Immunofluorescence Technology" pp. 27–36 (1982) found a 60% recovery using two pulses of 3 ms with a 3 ms (millisecond) dark interval. However, in many cases, recovery does not occur or only a partial recovery of the initial intensity occurs. Recovery is negatively related to the product of the excitation time and intensity of the exciting light and is positively related to the time the sample is left in the dark following excitation (Wick et al., *Ann. New York Acad. Sci.* 254, 172–174 (1975); Kaufman et al., *J. Histochem Cytochem.* 19, 469 (1971); and Schauenstein et al., *J. Immunol. Meth.* 8, 9–16 (1975).

2. Conventional light sources

Most fluorescence microscopes, i.e., those in hospital laboratories or those used for research, are equipped with either a halogen, a mercury or a xenon light source. The average laboratory can neither afford a laser excitation source nor has the personnel qualified to properly align the light source. In addition, laser light sources require that special low-fluorescence optics and filters be used to avoid autofluorescence of the optical system.

a. Mercury lamps

Nairn et al., *Clin. Exp. Immunol.* 4, 697–705 (1969) measured the fading of rat gastric cells stained with FITC-conjugated anti-human globulin using a HBO 200 W mercury lamp. When the specimen was mounted in buffered glycerol at pH 8.6 and excited with only ultraviolet light (UV), 35 s (seconds) were requied to fade half the initial intensity. When the sample was excited with UV+blue light, the half-life decreased to four seconds. After one minute continuous excitation with UV irradiation, only 30% of the initial intensity remained. Haaijman *Inst. Experim. Gerontol.* (1977) compared the fading of aminoethyl-Sephadex bound tetramethyl rhodamine isothiocyanate (TRITC) and membrane-bound TRITC. Membrane bound TRITC faded about 25% more in 2 minutes than the TRITC bound to the beads. He found the FITC and TRITC bound to aminoethyl sephadex beads faded less rapidly than cell-bound conjugates. Golden and West *J. Histochem. Cytochem.* 22(7), 495–505 (1974) measured the fading of Ehrlich's hyperdiploid mouse ascites tumor cell stained with acridine orange using a HBO 100 W mercury lamp. They described the fading in terms of a time constant, tau, which is approximately 1.8 sec. Although not specifically stated, it can be inferred from the fading curve that tau is the time required to fade to 37% of the initial intensity. The data showed that the fading can be approximated with a single exponential. The shape of this fading curve was dependent on the cell type and the substrate biopolymer.

b. Xenon lamps

Using a XBO 75 W xenon lamp, McKay et al., *Immunology* 43, 591–602 (1981) measured the fading of conjugates of anti-human gamma globulin-FITC and anti-human gamma globulin-rhodamine B 200 (RB 200). With the RB 200 conjugates, there was little, if any, fading after two min, and this decline could not be separated from instrument error. For fluorescein, however, there was considerable fading which reached a plateau after a certain period of time. This result ws interpreted to mean that fading is the sum of two components, one that decays exponentially and one that remains constant. They subtracted the plateau level value, which represents the non-fading component, from each intensity value and plotted the fading component vs time on semi-logarithmic paper. This plot produced a straight line which showed the fading obeyed first-order kinetics. They found a half-life of about 1 min for their FITC conjugates. Enerback and Johansson

*Histochem. J.* 5, 351-362 (1973) measured the fading of several fluorochromes including FITC and Feulgen-Schiff using a XBO 75 W xenon lamp and instrumentation capable of recording fluorescence of very short duration. They found a half-life of two 2 seconds for FITC under continuous excitation. For Feulgen-Pararosaniline reaction, there was a 20% loss of initial fluorescence after 20 seconds. They also tested the effect of repeated very short excitation times at two second intervals on the fading. For FITC, there was significant fading after fifteen measurements with illumination times up to 1/60 scond. Using an oscilloscope, they found a fading of 0.5% during the first two 2 ms of illumination. For Feulgen-Schiff stained cells, the fading could be prevented by reducing the illumination time. Bohm and Sprenger *Histochemie* 16, 100-118 (1968) measured the fading of sperm stained with several dyes, including acriflavin and Pararosaniline under 5 min continuous excitation using a XBO 150 W xenon lamp. They found a fading rate of 25% and 60%, respectively, for Pararosaniline and Acriflavin.

c. Recovery

McKay et al., *Immunology* 43, 591-602 (1981) tested the recovery of FITC-stained cells using a 75 W xenon bulb. They allowed the FITC conjugate to fade approximately 6 half-lives and then measured the intensity by varying the dark period between excitations using an excitatio shutter. They found that if the shutter was opened for only three seconds every five min., the intensity increased from 64 to 99 (33%). This recovery appeared real because it could not be obtained on unstained specimens. This data correlated with the recovery experiments performed using lasers.

Methods of Protection

In light of the above, the Applicants reached the conclusion that in order to improve the accuracy of the IF test and to achieve quantitation of the fluorescently emitted light, it is essential at least to stabilize the fluorescence emission. The Applicants, therefore, devised a chemical system to accomplish this result. The Applicants have also discovered that when selecting possible chemical agents to retard fading, it is important that the agents do not fluoresce at or near the excitation or emission wavelengths of the dye or chemical used. Considerations which must be made in proper selection of a fading retardant means would become clear from the following discussion.

Gill *Experientia* 35, 400-401 (1979) used sodium dithionite (DT) to inhibit the fading of onion cuticle cells labeled with fluorochromes such as fluorescein, acridine orange, 33258 Hoechst, Acriflavin and others under continuous excitation for two min with an HBO 200 W mercury bulb. It should be noted that Gill did not use these dyes conjugated to antibodies. Gill reported that for fluorescein and acridine orange, the intensity increased before starting to decrease after five min of continuous excitation. Gill's data showed that after normalizing the intensities, the ratio of the intensity at two min. excitation to the initial intensity was 0.67 for the buffer control and 1.00 for the mounting medium with DT.

Giloh and Sedat *Science* 217, 1252-1255 (1982) incorporated n-propyl gallate or 3,4,5-trihydroxybenzoic acid n-propyl ester (nPG) into the mounting medium to retard the fading during serial photographs of nuclei of fixed, cultured Drosophila cells incubated with a monoclonal antibody against *Drosophila melanogaster* embryo nuclei. It was found that 2 to 5% nPG in glycerol reduced fading of tetramethyl rhodamine isothiocyanate (TRITC) and FITC by a factor of 16 and 7 times, respectively. At concentrations of 10-20% nPG in glycerol, self-quenching occurred. It was also noted that free radical scavengers such as dithiothreitol (DTT) at concentrations of 0.05M to 0.2M in 90% glycerol had no effect on fading. Giloh and Sedat, supra suggested that the initial fluorescence intensity may decrease upon storage in nPG. The decrease in intensity can be reversed and prevented by washing the slides in phosphate buffered saline (PBS) and storing them in pure glycerol.

Johnson et al., *J. Immunol. Meth.* 55, 231-242(1982) added para-phenylenediamine (PPD) or triethlenediamine or 1,4 diazabicyclo[2,2,2]octane (DABCO) to the buffered glycerol mounting medium to reduce fading during examination of cells for ANA staining. Using a 16×Plnachromat objective and PPD at a concentration of 0.01M, they found that about 90% of the initial fluorescence intensity remained after 5 min. of continuous excitation with an HBO 50 W mercury lamp. DABCO provided similar protection when used at a higher concentration of 0.2M. When the magnification was increased to 40×/0.95, with both PPD and DABCO, there was about 60% of the initial intensity remaining after 5 min. continuous excitation. For the glycerol controls using the 40×/0.95 objective, only 10-20% of the initial intensity remained after 5 min continuous excitation. DABCO was recommended over PPD since the latter is a skin sensitizer, photosensitive and undergoes oxidative degradation.

Johnson et al., supra also compared the fading of stained nuclei in the presence and absence of protecting agents using an HBO 50 W mercury and an HBO 100 W mercury (incident illumination) and a Quartz-Iodine (QI) lamp with transmitted, darkfield illumination. The relative initial fluorescence intensities of the three lamps were 12:5:1, respectively, for HBO 100:HBO 50:QI. It was reported that at low magnification (16×A), the fading was similar for all three lamps.

An important point to note is that blank readings (unstained sections mounted in the same medium as the stained slide) accounted for as much as 25% of the readings on stained cells. The blank readings were subtracted from the corresponding reading from the stained sections. It was postulated that the blank reading accounted for the non-fading component described by McKay *Immunology* 43, 591-602 (1981). However, the blank readings that McKay used were on the stained slides from an area of non-specific staining. The values were much lower than 25%. Whether it is valid to use the unstained cells emission as a background for the stained cells was unclear. No data was given by Johnson et al to document that this is a true reflection of the amount of fluorescence intensity which the stained cells emit non-specifically. This is particularly important since the amount was so high relative to the specific intensity, and the counterstain was added to mask the non specific intensities. The counterstain emission itself is excluded by the filter selection.

As will be further described herein infra, it has been determined that mounting the specimen in a non-fluorescent resin reduces fading by stabilizing the macromolecule-dye complex. Rodriguez and Deinhardt *Virology* 12, 316-317 (1960) used polyvinyl alcohol to prepare semi-permanent mounting medium and to reduce fading upon storage. It was reported that slides stored at 4° C. and frequently exposed to room temperature for hours at a time did not show appreciable fading for periods exceeding nine months. Fukuda et al., *Histochemistry* 65, 269–276 (1980) stained smears of mouse hepatocytes with an anti UV-DNA antibody and FITC-labeled antibody and measured the fading in glycerin or buffeer with post fixation with methanol. After 20 min. continuous excitation, the fluorescence was nearly immeasurable. However, post-fixation of the specimen with absolute methanol for 1 hr followed by mounting in a non-fluorescent resin greatly reduced fading. The mechanism of this effect is most likely the removal of water with its component of dissolved oxygen. This provides more rigidity to the fluorophore complex and less opportunity to interact with oxygen which accelerates the fading rate. No detectable fading was found after storing the specimens 2 years at room temperature withoug shielding against light. McKay et al (1981) found that by mounting the specimen in pure glycerol or butanol instead of 15% glycerol, the quantum yield of RB 200 in solution could be doubled and the intensity of fluorescence of stained slides was increased by almost 50%. Again, this is consistent with the above mentioned mechanism of the decreased water concentration providing more efficient fading protection since alcohol is a dehydrating agent.

Fukuda et al., *Histochemistry* 52, 119–127 (1977); Fujita et al., *Histochemistry* 40, 59–67 (1974); Fukuda et al., *Acta Histochem Cytochem.* 9, 180–192 (1976); Fujita et al., *Histochemie.* 36, 193–199 (1973); Fukuda et al., *Acta Histochem. Cytochem.* 8, 331–341 (1975) used another method to eliminate fluorescence fading of the Feulgen-stained nuclei. They either pre- pr post-irradiated (after nuclear staining) the specimen for up to 20 hr to selectively remove the non-specific fluorescence and subsequently the stain retained the proportionality between DNA content and stain concentration. This method is based on the fact that the non-specific fluorescence decays faster than the specific fluorescence, therefore, by carefully adjusting the pre- or post-illumination time, one can selectively remove the unwanted fluorescence and not destroy the specific fluorescence. Fukuda post-fixed a pyrimidine-dimer FITC complex with ethanol and mounted the specimen in Entellan (a non-fluorescent mounting resin). The specimens were irradiated with violet light for FITC (405 nm) before or after staining, for five hr. They found that post-irradiation of the specimen with violet light for appropriate times after staining reduced background fluorescence and decreased the fading of tissue-bound FITC. Fukuda standardized the conditions for post-irradiation for DNA cytofluorometry on a paraosaniline Feulgen stained smear and found that a post-irradiation of 10 hr retained proportionality between DNA amount and fluorescence intensity. This method essentially accelerates the fading to a plateau level and thus provides minimal subsequent fading so that a more stable emission during measurement is obtained.

Because of the difficulty of comparing reports of the effectiveness of protecting agent when performed under various excitation and measurement conditions, the Applicants tookthe first step of testing the protective effects of several chemical reducing agents under the same excitation conditions. The agents compared were sodium dithionite (DT), dithiothreitol (DTT), dithioerythritol (DTE) and triethylenediamine or 1,4 diazabicyclo[2,2,2]octane (DABCO). The Applicants performed the testing using a macrofluorophotometer for screening the effectiveness and a microfluorophotometer for verifying the "in use" conditions. The kinetics of the fading curves were analysed and implications for elucidation of the mechanism of fading and the mechanism of the protection were determined. The instrumentation is described first. As is evident from the above, a standardized system or method of determining and quantifying FRP has simply not heretofore been known in the art. The Applicants now describe specific embodiments to achieve the desired results.

DESCRIPTION OF PREFERRED EMBODIMENTS

1. Instrumentation

A Zeiss microscope-photometer is adapted for epi-fluorescence (incident excitation) using an HBO 100-W mercury lamp with a stabilized DC power supply. FIG. 1 shows a schematic of the light path. A microprocessor, Zonax, is integrated with the microscope. A wide-band FITC filter set (Zeiss Product No. 487709) was used, excitation from 450 to 490 nm, dichroic mirror at 515 nm and barrier filter at 520 nm. The filters were mounted in the Zeiss III-RS illuminator filter holder which contained positions for four combinations. A heat filter (Heat reflecting CALFLEX, Zeiss product No. 467832) placed in the exciting path minimizes intensities from background materials and reduces fading. A linear interference monochromator is placed in the emission light path to the PMT.

Attached to the monochromator on the microscope is a Hamamatsu PMT (type R928 multi-alkali photocathode, 9 stage, side-on), powered by a stabilized high voltage power supply. An amplifier was built into the PMT housing. The emitted intensity was converted into a voltage displayed on the computer cathode ray tube (CRT) screen. A series of variable field stops can mask down the area of the specimen actually illuminated by the exciting light. They ranged from 0.05 to 2.5 mm diameter. Adjacent to the PMT, in the emission light path, are diaphragms that can vary the area being measured. They ranged from 0.08 to 5 mm diameter. The amount of fading during the measurements can be reduced by a fast shutter which excites the specimen for milliseconds. The microscope is equipped for brightfield, darkfield and phase contrast for localizing the specimen.

Software programs, commercially available and provided by Zeiss, control the microscope shutters, field stop, PMT diaphragm, high voltage, gain and the scanning stage. A measurement protocol either automatic or manual could be employed.

Quantitative endpoint determination requires stable emitters to calibrate the photometer unit. Suitable as stable emitters for photometer calibration purposes are any organic or inorganic particles coated or impregnated with any materials that are fluorescence emitters, such as $UO_3$, $Tb^{3+}$, $Eu^{3+}$ and the like.

Several types of fluorescent materials for use with microfluorometry for standardization were evaluated. Table 2 gives the suppliers, size, shape and the kinds of fluorescent emitters that were studied.

TABLE 2

CHARACTERISTICS OF FLUORESCENT STANDARDS

| Name | Mfg. | Material | Shape | Size | Fluorophore |
|---|---|---|---|---|---|
| Thread | NBS | Uranyl glass | Cylinder | $3 \times 4 \times 10\mu$ | Uranium oxide |
| Plate | Corning | Uranyl glass | Square Sheet | $5 \times 5 \times 0.3$ mm | Uranium oxide |
| Mount | Zeiss | Uranyl glass | Sheet | 5 mm. dia. | Uranium oxide |
| Phosphor | RCA | Inorganic elements | Irregular | Microns | Inorganic |
| Flurospheres | Coulter | Polystyrene | Sphere | 5 or $10\mu$ | Yellow dye |
| Covaspheres | Covalent | Latex | Sphere | $1\mu$ | Green dye (covalent) |
| Fluoresbrite | Polysciences | Latex | Sphere | 0.05 to $1\mu$ dia. | Yellow dye (covalent) |

The National Bureau of Standards (NBS), Gaithersburg, MD, provided 7-to-20 micron diameter threads of uranium-impregnated glass spun to achieve these small diameters; these fibers give uniform fluorescence throughout their length. The wavelengths of the excitation and emission peaks are 423 nm and 534 nm, respectively. Microscope slides were prepared by cutting the threads into fragments and using those that approximated the size of the bacteria of interest.

A glass filter plate (Corning Glass, Inc., Corning, NY catalog No. 3718) consists of glass impregnated with uranium that fluoresces yellow-green. Also, a sheet of uranyl glass, provided by Zeiss, Inc., is mounted by magnetic attachment to the objective for easy removal.

Inorganic phosphor particles including sulfides or silicates, (RCA Corporation, Lancaster, PA), 1 to 10 microns, are used for cathode ray tube screens. These particles can be selected to approximate the emission wavelength of the fluorophore of interest, such as FITC. They do not fade with continuous excitation and, when mounted dry, are stable for many years and can be used as stable emitters.

Fluorospheres (Coulter Electronics, Inc., Haialea, FL) are polystyrene spheres that have a fluorophore incorporated into the plastic. They are available in 5- or 10-micron-diameter sizes. The 10-micron spheres are also available in various fluorescent intensities ranging in arbitrarily assigned values from 0.02 percent to 100 percent. This is achieved by adding proportionate amounts of dye during the manufacturing stage. The wave lengths of excitation and emission are 460 nm and 550 nm, respectively. Decay is less than one percent per year if the fluorospheres are stored in a cool, dark place.

Polysciences, Inc., Warrington, PA, provides latex spheres, Fluoresbrite, in sizes ranging from 0.05 to 1.00 microns in diameter. The recommended shelf life is one to two years. These spheres can also be coupled to antibodies or other proteins. The excitation and emission maxima are 458 nm and 540 nm, respectively, for the spheres with the yellow-green dye.

Covaspheres (Covalent Technology Corp., San Jose CA) are latex spheres that are uniform in size, approximately one micron in diameter, and available with red or green fluorescing dyes. The user may link these covalently to immunoglobulins or other protein. The excitation and emission peak wavelenghts for thegreen covaspheres are 468 nm and 537 nm, respectively.

Baltimore Biological Laboratory, Cockeysville, MD, has a microscope slide that incorporates three different inorganic phosphors intto a semipermanent, non fluorescent mounting media. One phosphor emits yellow-green light and one emits red-orange light. They do not fade under repeated excitation and have a shelf life of many years.

Mounting Media

All the standard materials are measured mounted in very, very low fluorescent oil from R.P. Cargille Lab, Cedar Grove, NJ. This oil is loaded into a disposable plastic syringe fitted with a micropore filter and needle. When used for preparing slides, an amount is pushed through the filter onto the slide, thus ensuring a particle-free, non fluorescent background.

For the experiment with various mounting media, Entellan (E. Merck, Darmstadt, Germany), Flo-Texx and Pro-Texx, (Lerner Laboratories, Stamford, CT), or phosphate-buffered glycerol with a pH of 8.2 was used.

Field Measurement Optimiation

Figure 2:
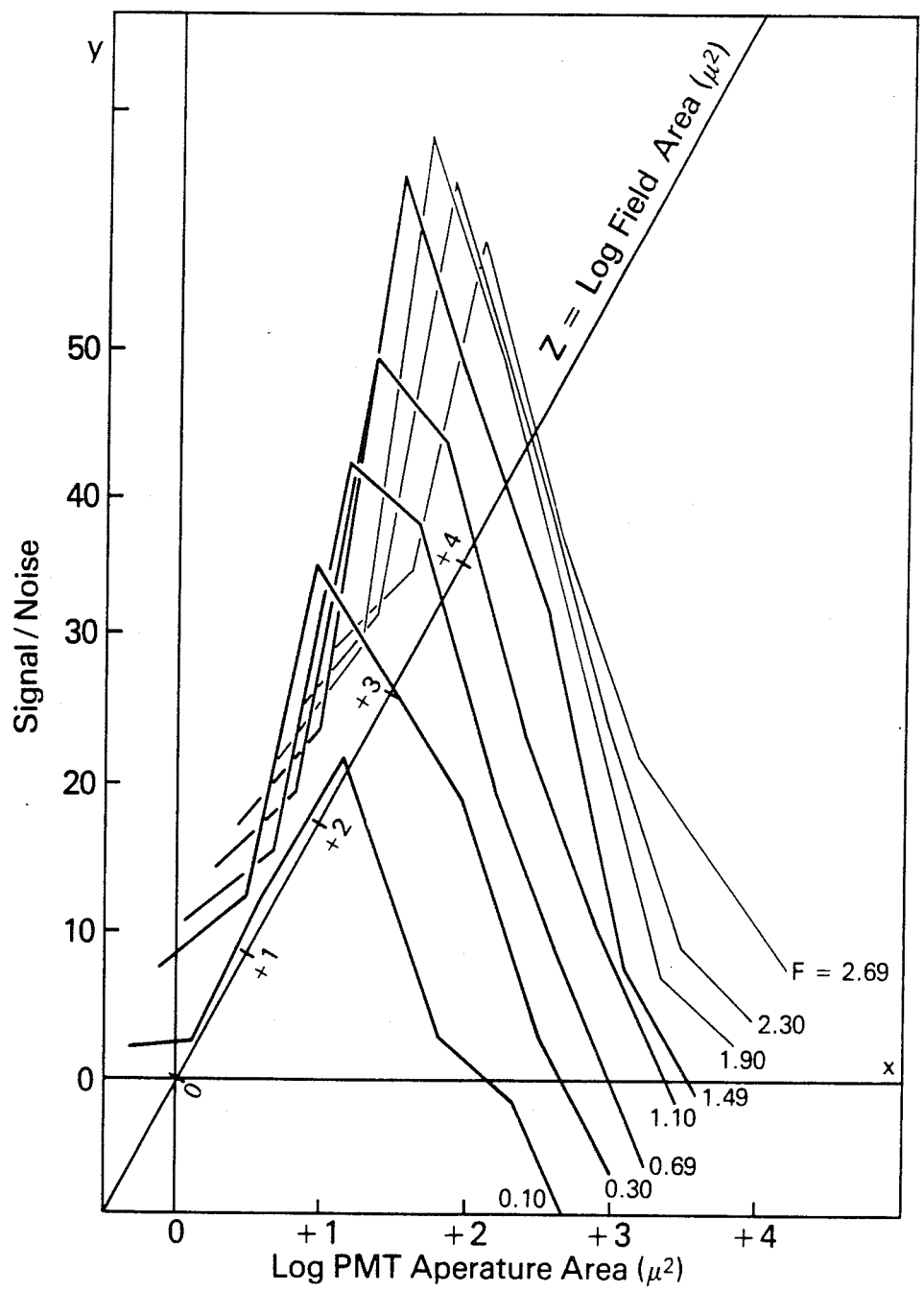
FIG. 2 shows three dimensional graph of the signal to noise ratio versus illuminating field area and PMT aperature area of a fragment of NBS thread.

FIG. 2 presents the results from varying the area illuminated by the exciting light and the area sensed by the PMT. The signal-to-noise ratio is the intensity from a uranyl glass fragment approximating a representative bacterium area in ratio to an adjacent non fluorescent area accounting for background. This value is plotted versus the illuminating field area and the PMT aperture area as a three-dimensional graph. In this experiment, a fragment of NBS thread of $3 \times 4$ microns was measured. Using both 0.63-mm-diameter field and PMT diaphragms, produced the optical signal-to-noise ration. The projected image of these diaphragms corresponded closest to the projected image of the uranyl fragment area.

Instrument Performance

The plate was used in evaluating the reproducibility of the microscope-photometer. Under continuous excitation, a slope of $-0.008$ percent per second of the linear regression line and a coefficient of variation of 0.313 percent (Table 3) was obtained.

TABLE 3

Reproducibility of Fluorescent Standards

| STANDARD | INTENSITY | VARIATION (CV %) | STABILITY (Slope %/sec.) |
|---|---|---|---|
| Plate | 14.95 | 0.3 | −0.008 |
| Phosphor | 39.30 | N.A. | −0.030 |
| Fluorospheres | 1.49 | 5.2 | −0.030 |
| Fluoresbrite | 1.79 | 11.0 | −0.100 |
| Covaspheres | 3.28 | 30.0 | −0.300 |

Linearity Determination

Figure 3:
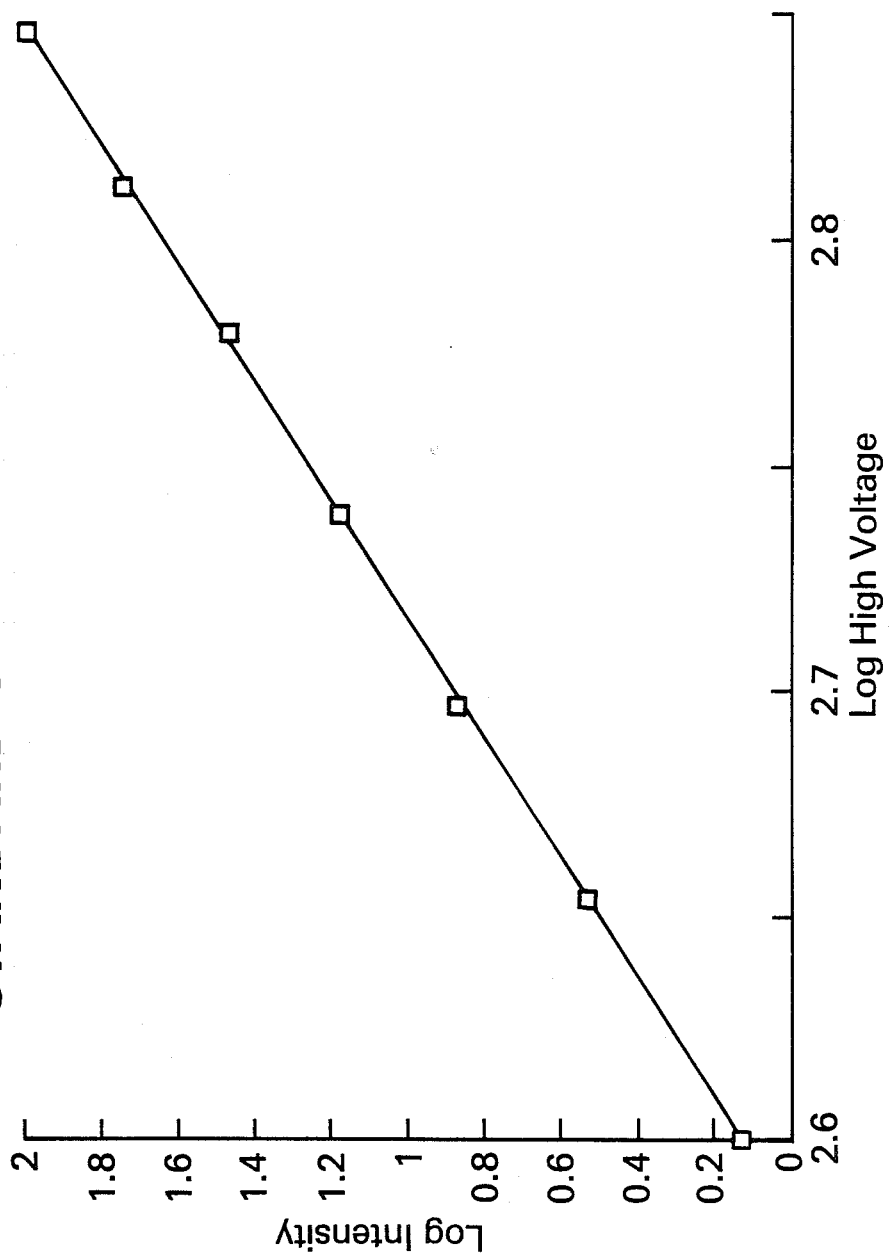
FIG. 3 shows correlation of the corrected fluorescent intensity readings of the thread with high voltage settings.

To determine that readings were within the instrument's linear range, the intensity of a thread fragment was measured employing all usable combinations of gain and high voltage and using the optimal field and the PMT diaphragms. FIG. 3 shows a plot of the corrected fluorescent intensity readings of the thread versus the high voltage. Multiplying the voltages by the gain settings of the PMT amplifier corrected the fluorescent intensities.

Calibration Curve

Figure 4:
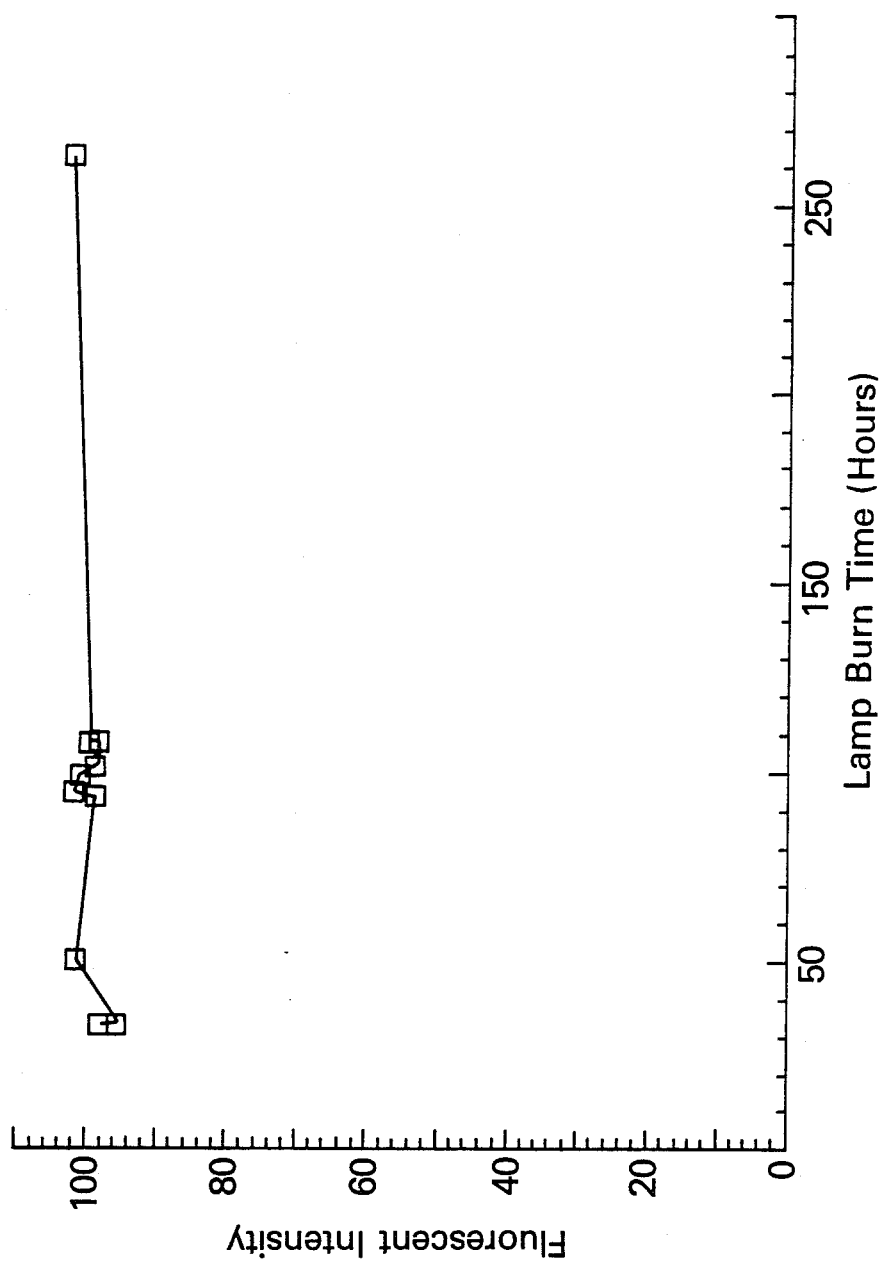
FIG. 4 shows fluorescent intensity of Corning plate versus burn hours of one 100 W mercury lamp over a period of three months.

To establish daily intensity readings comparisons, the fine focus of the microscope was used to adjust the PMT output to a maximum. FIG. 4 shows the intensity readings for the daily settings of the plate during 240 hours with the same 100-W mercury lamp. Readings were taken at various amplification settings (high voltage and gain). The regression line parameters (slope and intercept) adjust the PMT voltage readings to comparable values to correct for aging effects of the excitation lamp or other variables. Table 4 gives the parameters of several regression lines for five lamps at various burn hours.

TABLE 4

Characteristics of Standard Calibration Curves at Various Burn Hours With Different Lamps.

| LAMP # | BURN HOURS | REGRESSION LINE | |
|---|---|---|---|
| | | Slope | Intercept |
| 3 | 43 | 7.51 | −19.34 |
| 3 | 330 | 7.54 | −19.49 |
| 4 | 7 | 7.62 | −19.69 |
| 4 | 24 | 7.71 | −19.97 |
| 5 | 14 | 7.63 | −19.75 |
| 6 | 100 | 7.51 | −19.16 |
| 6 | 172 | 7.49 | −19.33 |
| 7 | 3 | 7.57 | −19.09 |
| 7 | 34 | 7.56 | −19.15 |

Having established the performance characteristics of the instrument, various standard materials were then evaluated.

Standards Performance

Figure 5:
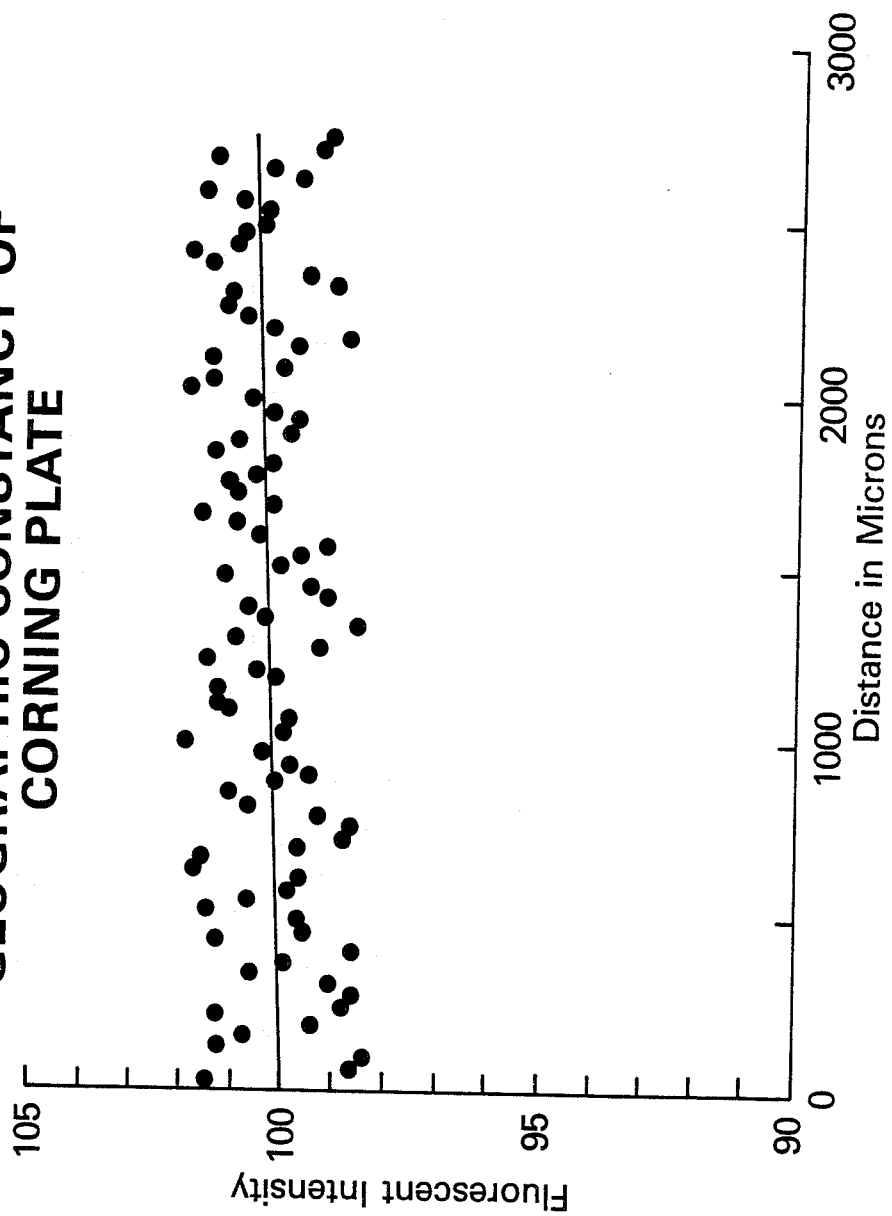
FIG. 5 shows scatter plot of fluorescent intensity versus distance moved in microns across Corning plate showing linear regression line.

The plate was tested for uniformity. The surface was scanned in 30-micron increments. FIG. 5 is a typical scatter plot of the fluorescent intensity as a function of the position on the plate. Shown also is the linear regression line, which has a slope of +0.026 percent per micron. The coefficient of variation of the mean is 0.9 percent.

Figure 6:
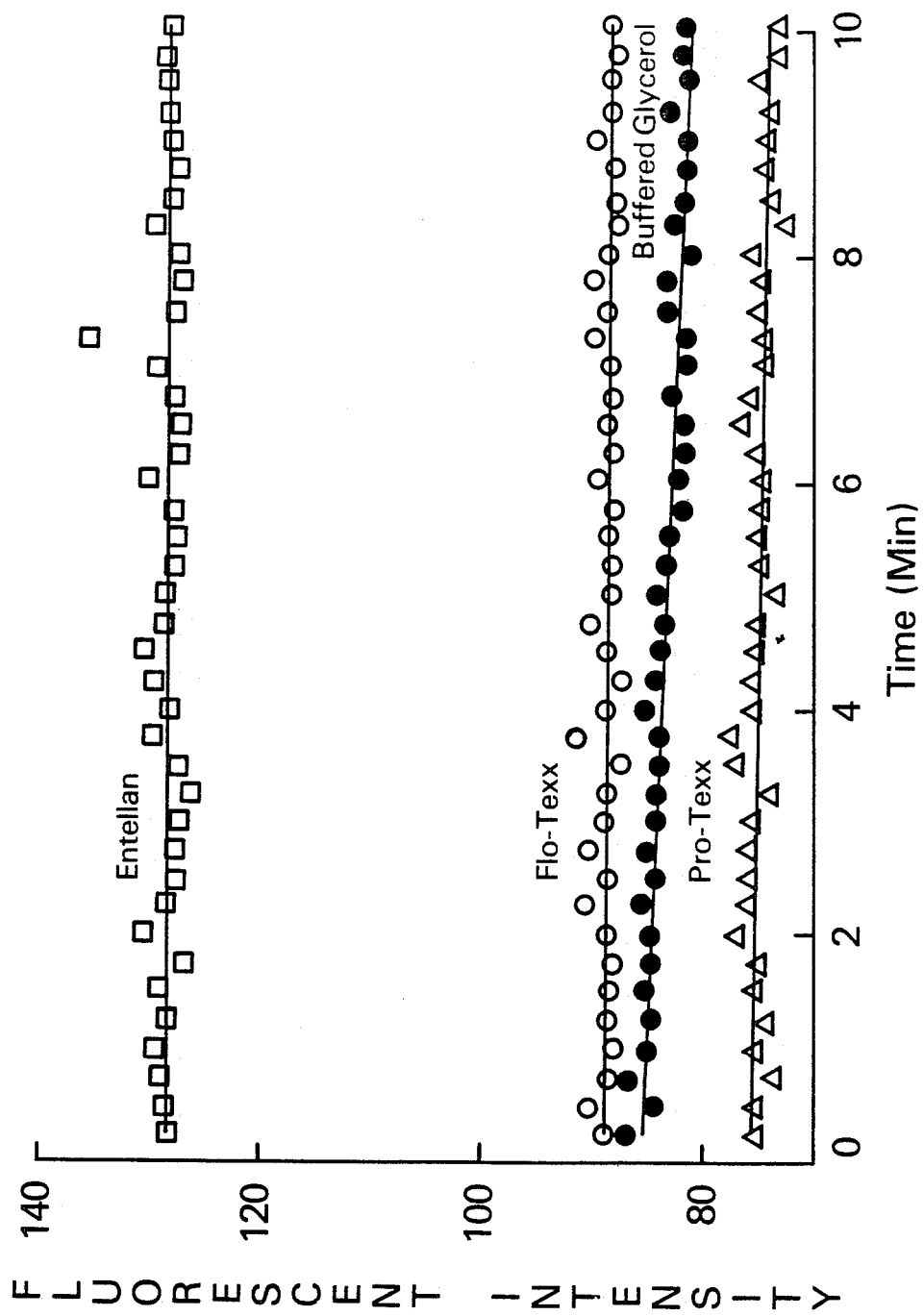
FIG. 6 shows stability of phosphor particles in various mounting media under continuous excitation.

FIG. 6 shows intensity from the phosphor particles under continuous excitation. They were mounted in various mounting media on the microscope slide. The slopes (in percent per second) of the regression lines are +0.03 in Entellan, −0.05 in Flo-Texx, −0.18 in Protexx and −0.46 in buffered glycerol.

Figure 7:
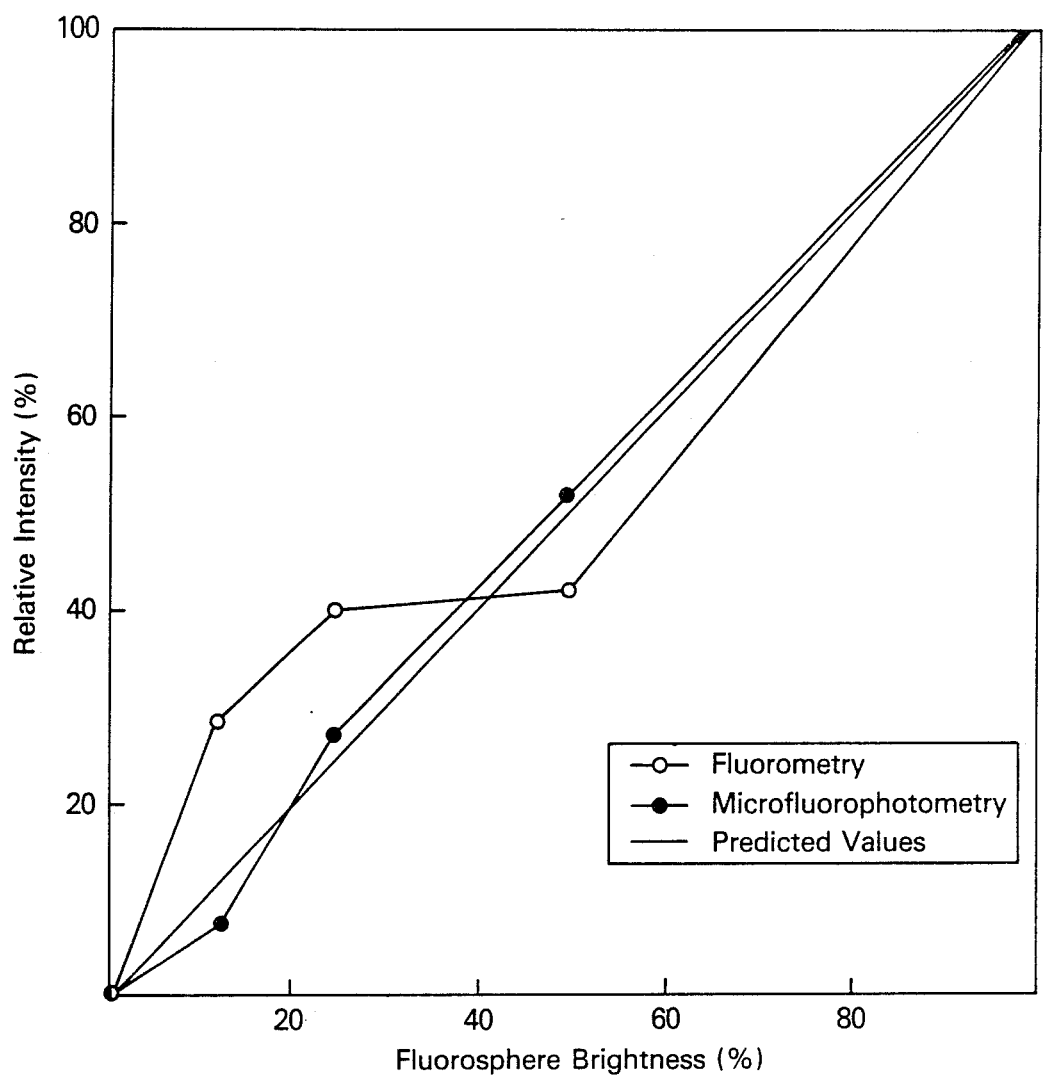
FIG. 7 shows comparison of measured intensity of fluorospheres with brightness based on dye concentration.

One drop of a 1:800 dilution of the graded fluorosphere stock materials was addd to glass slides, resulting in approximately one particle per oil immersion field (×1000). FIG. 7 gives the measured intensity values and the expected values based on the manufacturer's dye concentration used for the graded brightness fluorospheres. The measurements are consistent with the expected values measured by microscopy, whereas values by fluorometry deviate from the expected in several cases.

The fragments made from the NBS thread have intensities and size in the range of the bacteria expected to be of interest using these techniques.

Table 3 shows the intensity and reproducibility of some fluorescent emitters. For the last three emitters the coefficient of variation is calculated by taking repeated millisecond exposures on 20 different particles. The stability is shown by the slope of the linear regression line based on readings under continuous excitation.

Field Measurement Optimization

Optimizing the signal-to-noise ratio for the fluorescence measurement of small particles on a glass microscope slide showed that the highest value was obtained when the area illuminated and the area sensed corresponded to the particle area. Minimal but measurable errors from glare or scatter in this system occurred for other size areas. Thus, the minimal area that includes the entire particle is the optimal condition for measurement.

Instrument Performance

Fluorescent reproducibility depends more on stability under repeated excitation than on instrument fluctuation. Because repeated measurements are easily made with the semi-automated instruments, resulting in reduced variation, a less than one percent coefficient of variation can be achieved with this system if the emitter is stable. The number of measurements required varies depending on the brightness of the sample and should be determined for each type of biological material used.

The geographical non-uniformity of each of the uranyl glass plates shows less than one percent coefficient of variation, therefore any position on the plate can be used for calibration. Care must be exercised in cleaning the plates. Glare effects necessitate avoiding the edges.

A minimal slope of the linear regression line indicates stability. The instrument's characteristic slope is 0.008 (Table 3); therefore, any greater slope is presumed to indicate the emitter's fading.

Linearity Determination

The instrument response is proportional at various high voltage settings, and gains and the entire usable instrument's range gives accurate readings as described by a correlation coefficient of r=0.991.

Calibration Curve

Daily readings of the uranyl plate (FIG. 4) over the life of an HBO 100-W mercury lamp indicate stability of the excitation source. If any factors are believed to affect the intensity of the sample readings, these are compensated for by mathematical adjustment based on the plate readings. This allows accuracy in making comparable readings over long periods. Readings taken with different lamps may also be constant (Table 4); however, sufficient number of lamps have not yet been used to verify this completely. Using the characteristics (slope and intercept) of the regression lines from the calibration curves allows comparing the performance of each lamp at various burn hours. Table 4 indicates negligible changes between lamps and burn hours.

Standards Performance

Each of the materials has an excitation/emission spectrum suitable for use as a standard for FITC, although no one material has the exact excitation/emission spectrum of FITC. The size distribution accommodates the range of interest for use with various species of bacteria as well as tissue cells.

Because the geographical intensity variation is acceptable, i.e., less than one percent, either uranyl plate can be used daily for calibrations of the instrumentation. This can be done without searching for the same area on the plate, since any area gives the same intensity within one percent. Therefore, voltage reading at any random plate location is adjusted to maximum intensity with the microscope focus. This compensates for the effects of aging on the excitation lamp and of other variables.

The graded brightness fluorospheres are useful in checking the linearity of the measurement system and in selecting a standard of the required brightness within the range of interest. The spheres are convenient to handle, and slides can be prepared with one particle per field. This allows testing the effects of glare on the intensity measurements.

The daily fluctuations of the uranyl fragment are small. Therefore, this type of standard is stable and also suitable for compensating for the aging of the lamp. However, it is more tedious to locate the fragment than focus on the plate.

The emitters have excitation and emission spectra compatible with most types of instrumentation that are used for FITC measurements.

The phosphor particles are irregular in size, and therefore no comparison of individual intensities for use as fluorescence source standards is meaningful.

A larger variation in fluorescent intensity occurs with the covaspheres and the fluoresbrites. These particles are much smaller than others, which may account for the difficulty in achieving less variability.

The slope of the intensity measurements of the plate, phosphors and fluorospheres are within the variation of the instrumentation, therefore fading is not considered measureable with these emitters. The covaspheres and fluoresbrite show a degree of fading that may be bothersome only in some applications. Using a narrower band pass filter (440–490 nm) results in reduced fading of covaspheres, i.e., a slope of 0.10 percent per second. This filter may be used with FITC-containing materials. The covaspheres and fluoresbrite do provide a particle that can be covalently coupled with a specific antibody. Further, they may provide a model for the fading of fluorophores.

In summary, of the types of calibrators considered, each is useful for different purposes. The uranyl, glass materials have the greatest stability, being stable under continuous excitation and can be used to set values for the instrument. The inorganic phosphors are also suitable for calibration since they are stable with continuous excitation. Their irregular size however, causes intensity variations and thus can only be used if particular particles are selected. The fluorospheres are available in graded intensities and sizes and can be used to approximate bacteria type particles. The covaspheres and fluoresbrites can be bonded to an antibody, the latter being available in the smaller size range.

Using the uranyl glass plate or the magnetically mounted plate allows comparison of daily intensities produced by the microscope system and accounts for effects from the lamp and its aging. Use of regression line parameters allows monitoring variability.

Consistency can thus be obtained in values for fluorescent intensity measurements that enables interlaboratory comparisons and standardization.

As described herein supra, one of the most reliable of the calibration standard was the uranyl plate (Corning, Product No. 3718). By special order, a modification of this uranyl plate was provided in the shape of a microscope slide. The slide was found to be non-fading and thus was used to evaluate the stability of the microscope-photometer. Under continuous excitation for three hours, a negligible slope of −0.008 percent per second of the linear regression line and a coefficient of variation of 0.313 percent was obtained.

Using the uranyl glass slides with the optimal field stop and PMT diaphragms, the fluorescence intensity values were determined using all possible combinations of amplifier gain and high voltage settings which result in measureable intensities. Multiplying the readings by the gain settings of the PMT amplifier for each high voltage setting corrected the readings for various gain settings. The corrected intensity-voltage relationship was linear on a log-log plot. This indicates that the intensity is related to the high voltage as a power function, as is expected. The equation for this was $\log(\text{PMT output}) = (7.5) \times \log(\text{high voltage}) - 19.34$.

To compare intensity readings day-to-day, the uranyl glass slides were read before and/or after each experiment. Since the uranyl slides contain nothing upon which to focus, the focus knob was adjusted until the highest intensity reading was obtained. The maximum intensity was constant across approximately one half of a turn of the fine focus knob, indicating that the focal level on the uranyl glass slide is not critical within this amount and allowing confidence in the readings. Since the uranyl slide contains fluorophore throughout its entire thickness, it is assumed that the focal level of maximum intensity represents where the focal cone is filled with fluorescence from a solid angle relative to the numerical aperture of the objective used. An alternative method has been suggested, to scratch with a diamond point a mark on the surface of the glass and to focus on the mark. This however, is not satisfactory for two reasons: the scratch is hard to find and often disappears when oil of certain refractive index is added to the slide; also, the focal level is at the surface of the slide and since there is no fluorophore above the surface, small variations in focus will introduce large variations in the amount of light measured. The initial reading of the uranyl glass slide was set to 100 for ease of mathematical manipulation and to make full use of the graphics screen on the CRT. The high voltage was 517 volts and the amplifier gain was one. All further readings of both standards and samples were made at high voltage and gain settings that gave relative intensity values close to 100. Then these high voltage and gain values were used to correct the intensity readings of the sample relative to the uranyl glass slide reading for the day. This was done using the regression line parameters to calculate the extrapolated intensity at the standard settings of 517 and one.

c. Perkin Elmer calibration

The Perkin-Elmer 650-40 Spectrophotofluorometer is microprocessor-controlled and includes software to correct the sample fluorescence spectrum by reference to the emission spectrum of RB 200. This is actuated by setting the corrected mode after running the RB 200 spectrum. The fluorometer uses a second photodiode to automatically correct the dynode voltage for fluctuations caused by the light source which is a 150 W Xenon lamp with stabilized power supply. This is actuated by setting the ratio mode. The fluorescence intensity readings are displayed in digital form on the fluorometer display. Another software option allows repeated scanning of the fluoroescent specimen between pre-selected wavelengths and an average curve to be drawn from the individual curves.

2. Reagents a. Reducing agents

The chemical reducing agents tested were: sodium dithionite (DT, sodium hydrosulfite), Aldrich Chemical Company, Milwaukee, Wis., catalog #15,795-3, dithiothritol (DTT), Sigma Chemical Company, St. Louis, Mo., catalog #D0632; dithioerythritol (DTE), Sigma Chemical Company, catalog #D8255; DABCO (1,4 Diazabicyclo [2.2.2] Octane), Aldrich Chemical Company (catalog #D2,780-2) and n-propyl gallate, Sigma Chemical Company (catalog #P3130).

DT, DTT and DTE were prepared as stock solutions containing 0.5M reducing agent in 0.5M TRIS buffer, pH 8.2, (Trizma base, Sigma Chemical Company, product #T-1503). Stock solutions were aliquoted and frozen for future use to preserve the potency of this material. For use in the Perkin Elmer macrofluorophotometer, doubling dilutions of the reducing agents were prepared in the concentration range 0.5M to 0.063M in 0.05M TRIS, pH 8.2. The diluted reducing agent was then diluted 1 part reducing agent to 9 parts of a mixture of 0.05M TRIS pH 8.2 and FITC-labeled conjugate. For experiments in the Zonax microscope, dilutions in the range 0.25 to 0.5M were prepared. One part of the concentrated reducing agent was added to 9 parts buffered glycerol mounting medium.

For DABCO, doubling dilutions at a concentration range of 0.03 to 0.5M were prepared in 0.5M TRIS, pH 8.2 for determination of the optimal concentration and a final concentration of 0.3M in buffered glycerol was obtained by diluting a stock solution for other experiments.

b. Conjugates

The following FITC-labeled conjugates were used: Goat anti-human polyvalent globulin to Rubella virus with rhodamine counterstain incorporated (ENI, Columbia, Maryland); Goat anti-human polyvalent globulin with rhodamine counterstain incorporated for ANA (ENI); Goat anti-human IgG (heavy and light chains) with Evans blue counterstain for *Toxoplasma gondii* (ENI); Goat anti-human polyvalent globulin without counterstain incorporated (Centers for Disease Control, (CDC), Atlanta, Ga.) for *T. gondii*; *Neisseria gonorrhoeae* rabbit anti-human (IgG) globulin FITC conjugate with and without rhodamine counterstain.

3. Methods a. Measurement of fading in macrofluorophotometer

The fading of FITC-labeled conjugates (without added cells) with varying concentration of reducing agent present was measured in the Perkin-Elmer fluorometer and compared to controls. The following conjugates were measured: *T. gondii* (without counterstain) and *N. gonorrrhoeae* (with and without rhodamine counterstain). The excitation and emission wavelengths used were, respectively, 498-nm and 522-nm. The slit widths for excitation and emission, respectively, were 20-nm and 5-nm. The samples were continuously excited with a 150-W Xenon light for 10 min and intensities integrated for 15 sec intervals using the corrected spectrum option and a plot of corrected intensity versus time was prepared.

b. Measurement of fading in microfluorophotometer

Measurement of the fading in the Zonax microscope was done on the kits for ANA, Rubella and Toxoplasma. The IF microscopy slides from commercially available kits were prepared according to each manufacturer's directions except that an optimum concentration of reducing agent was incorporated into the buffered glycerol mounting medium provided with the kit just prior to mounting the slides. Whenever possible, the cells were located under transmitted visible light in order not to allow fading of the specimen. The high voltage and the amplifier gain to the PMT were adjusted so that the initial intensity would be 100%. The sample was continuously exposed to excitation light using a wide-band FITC filter combination (Zeiss product No. 487709) and intensity measurements were automatically taken every 0.1115 min for 10 min. using the kinetics software. A KP-560 bandpass filter was placed in the emission path to eliminate red emission light. The fluorescence intensities were later corrected to a standard high voltage and gain, based on the statistical regression parameters of the uranyl glass slide used to calibrate the instrument daily, to allow direct comparison of cell intensities independent of high voltage and gain settings and daily lamp fluctuations. Background readings were taken using the same filter combination as for the samples by measuring an adjacent area of the stained tissue or cells that showed the non-specific staining using the same diaphragm areas. The background readings were usually less than 1% of the sample readings. The background readings were subtracted from the readings of the specific intensities.

c. Statistical Analyses

One of the software packages available with the Zonax allows the generation of kinetics graphs (a graph of intensity over a user-predetermined time frame). The kinetics plot allows one to look directly at the percent fading of the sample. The software also calculates the coefficient of variation (CV%) which allows comparison of the fading of the cells independent of the mean. Use of a data link between the Zonax and an IBM host computer allowed generation of a variety of statistical analyses including regression, analysis of variance and graphics output from the original data generated by the microscope.

C. RESULTS

1. Selection criteria

DT, DTT, DTE and DABCO were tested to determine if they could effectively protect the FITC-labeled cells from fading. These agents were evaluated on the basis of five criteria:

a. Effective protection of the sample from fading.
b. No inhibition of the initial fluorescence intensity of the fluorophore.
c. No increase in the background fluorescence.
d. Able to function with the buffer, pH, molarity and temperature used with the mounting medium in the fluorescence test kits.
e. Practical to use.

The Perkin-Elmer Spectrofluorophotometer was used to screen the reducing agents for their protective ability. The fluorometer has the advantage of allowing rapid screening of the prospective agents without requiring several hours to prepare IF microscopy slides.

2. Buffer type

Any suitable buffer capable of buffering in the pH range of about 6.6 to 9.4, preferably in the pH range of about 7.5 to 8.4 can be used. Glycine adequately buffers in this range but has a high background intensity (autofluorescence). TRIS buffer maintains the pH within the desired range and does not significantly autofluoresce at the excitation and emission wavelengths used. PBS did not adequately buffer the reducing agent solution and was, therefore, not used further.

3. Buffer concentration

Experiments were performed to determine the lowest concentration of TRIS buffer that was still capable of holding the pH of the reducing agent at about 8.2 A 2.0M stock solution of DTT was diluted in TRIS buffer solution ranging from 0.2M to 0.02M and the pH of the solution was measured. 0.05M TRIS was the lowest concentration of TRIS capable of maintaining a pH of 8.2 (see Table 5).

TABLE 9

| hz,1/32 OF BUFFER CONCENTRATION FOR DITHIOTHREITOL | | | | |
|---|---|---|---|---|
| Concentration | 0.20 M | 0.10 M | 0.05 M | 0.02 M |
| Tris(hydroxymethyl) | | | | |

TABLE 9-continued

| | hz,1/32 OF BUFFER CONCENTRATION FOR DITHIOTHREITOL | | | |
|---|---|---|---|---|
| Concentration | 0.20 M | 0.10 M | 0.05 M | 0.02 M |
| aminomethane | | | | |
| pH | | | | |
| with 0.2 M DTT | 8.38 | 8.24 | 8.14 | 8.03 |
| without DTT | 8.38 | 8.25 | 8.21 | 8.11 |
| Background Intensity (Relative Light Units) | | | | |
| with DTT | 15.93 | 10.83 | 10.72 | 10.66 |
| without DTT | 18.77 | 14.19 | 12.57 | 10.20 |

4. Reducing agent concentration

Figure 8:
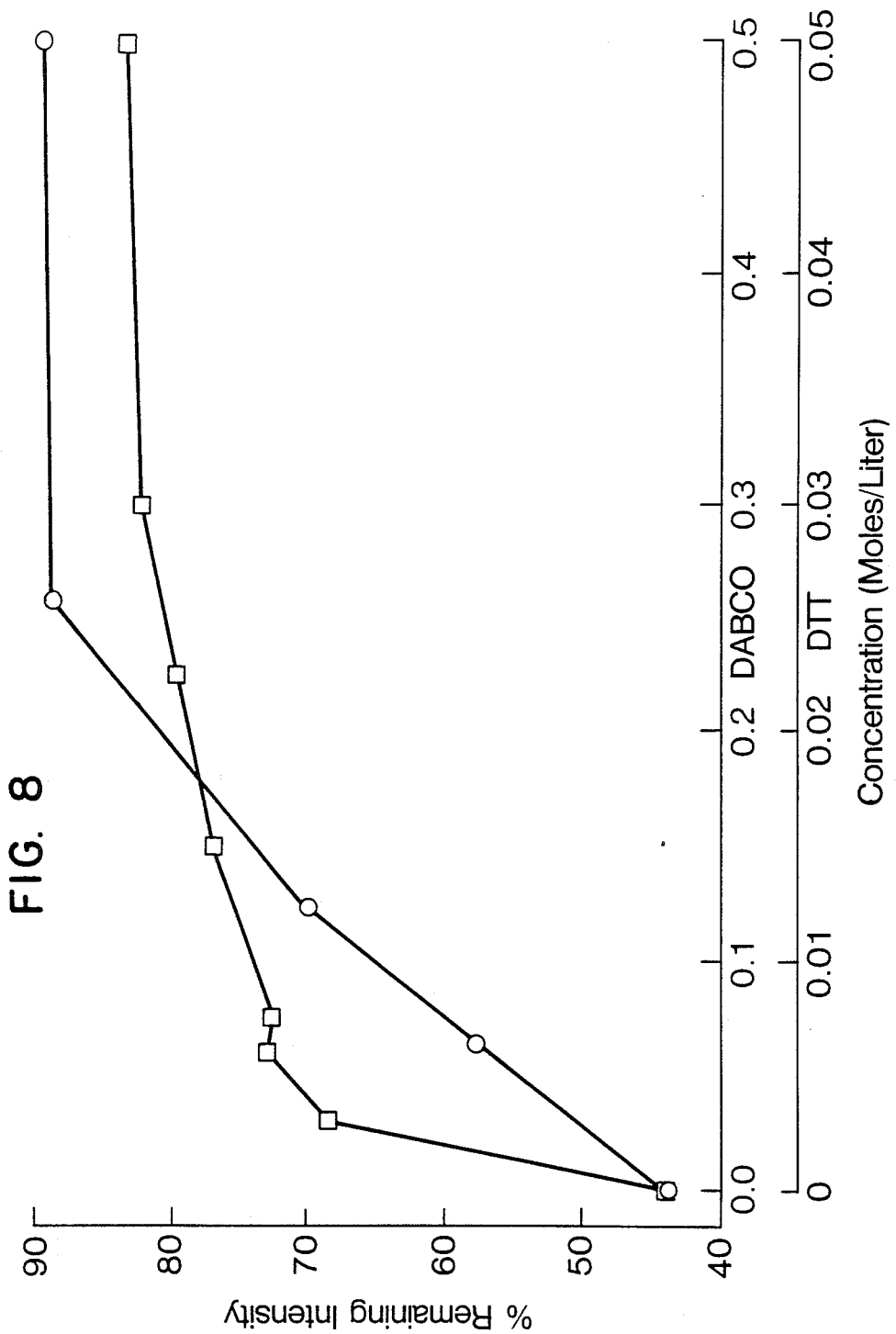
FIG. 8 shows the relationship of optimization of reducing agent concentration for protection from fading of FITC-labelled antibodies after 30 min excitation, the % remaining intensity in the Perkin-Elmer is plotted vs the reducing agent concentration in moles/liter. DABCO was tested on *Rubella* conjugate (open squares) and the DTT was tested on *Toxoplasma gondii* conjugate (open circles).

Various concentrations of reducing agents were added to a constant volume of rehydrated FITC-labeled conjugates. The percent remaining after 30 min excitation (readings taken every min) in the Perkin Elmer is shown in FIG. 8. Data are shown for DABCO with Rubella antibody and DTT with Toxoplasma antibody. DTT or DTE shows the most protection of the agents tested when used at their optimal concentration of 0.033M. It is noted that the optimal concentration for DABCO is 0.3M, which is the same as recommended by Johnson, et al. 1982. This is a concentration which is ten times higher than that used for the other agents. Table 6 compares the fading of the FITC-conjugate after 10 min continuous excitation at the optimal concentrtion for each of the reducing agents DABCO, DTT and DTE. The error around each measurement was less than 1% and does not show up on the graphs. A 10 min measuring period was chosen over the previously used 30 min period in order to make the times more compatible with those used in the microscope and those that might be used in a clinical laboratory.

TABLE 6

| SELECTION OF OPTIMAL REDUCING AGENT IN MACROFLUOROPHOTOMETER | | | |
|---|---|---|---|
| | DTE | DABCO | Unprotected |
| Background Intensity in 0.05 M TRIS | 25.5* | 25.7 | 5.7 |
| Optimum concentration in 0.05 M TRIS | 0.033 M | 0.3 M | not appl. |
| Conjugate: | | | |
| Initial intensity minus background | 1049.3* | 701.5 | 1049.3 |
| 10 min intensity minus background | 918.4 | 654.5 | 726.3 |
| % Remaining intensity based on initial intensity | 87.8% | 94.0% | 69.0% |
| % Remaining intensity based on unprotected initial intensity | 87.8% | 64.5% | 69.0% |

*Relative Intensity Units

5. Microscopic verification of protection

After suitable protecting agents were found by screening in the macrofluorophotometer, the protective ability of these reagents was verified by incorporating the reducing agents into the mounting medium of the IF microscopy slides.

Figure 9:
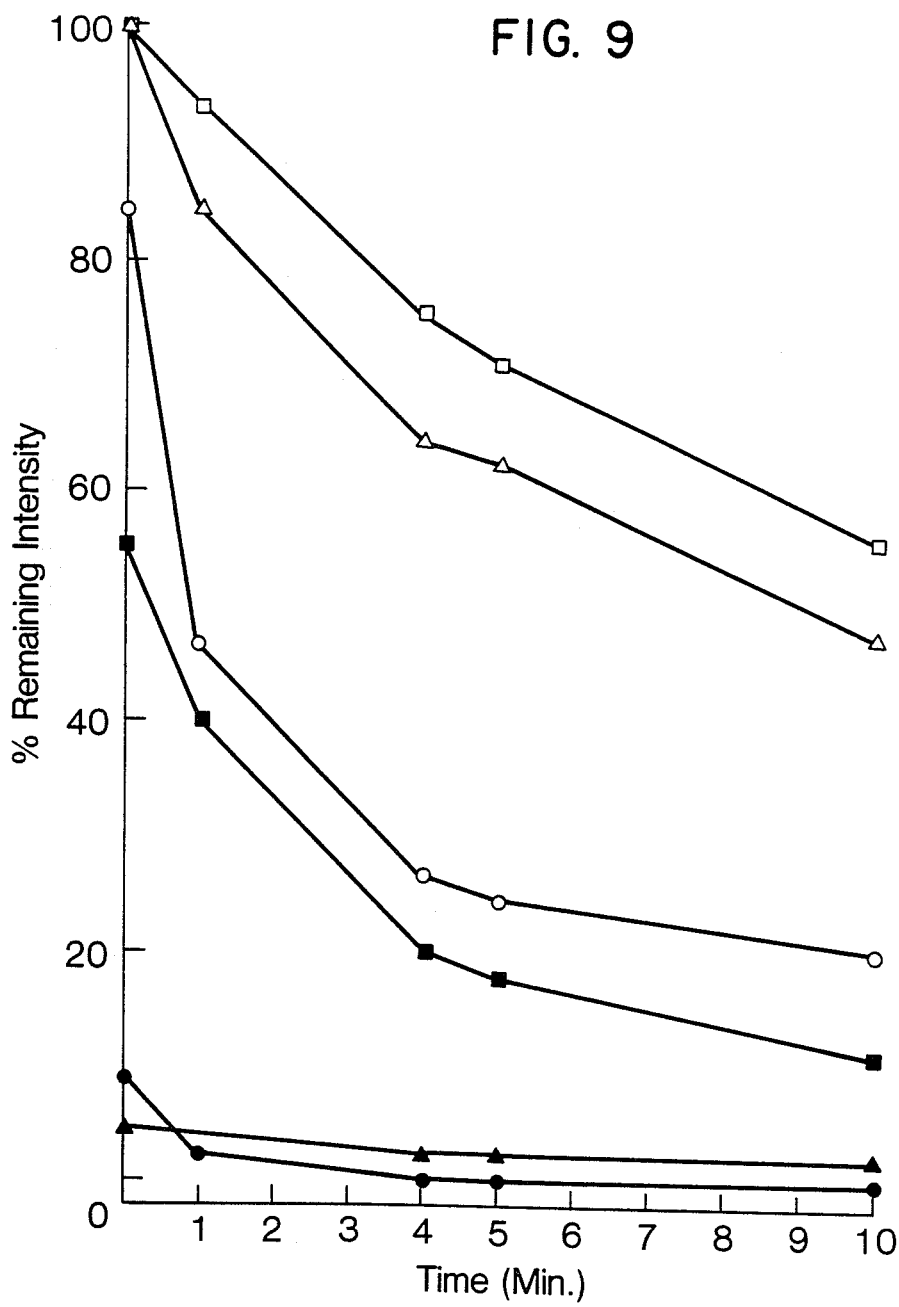
FIG. 9 shows the relationship of fading of cells on test kit slides with and without 0.025M DTE added to buffered glycerol mounting medium, the % remaining intensity is plotted vs time in min for *Toxoplasma* (squares), Rubella (triangles), and ANA (circles) with DTE (open) and without any reducing agent (solid).

FIG. 9 is a plot of percent remaining intensity after 10-min continuous exposure to excitation light, with and without reducing agent present. Shown are results with Toxoplasma, Rubella ana ANA test kit slides mounted in kit buffered glycerol with or without 0.025M DTE added. Since the labeled specimen fade too rapidly to record the initial, unfaded intensity, the first possible intensity (within each kit) which is the reading with the highest intensity, is used as the initial intensity. It should be noted that in the case of ANA and Rubella, unprotected, only 8 and 5%, respectively, of the protected intensity remained after 0.1 min. The initial intensity with DTE was 10 times greater than the unprotected intensity. It may also be noted that when visually observing the cells without DTE, the cells were totally red (due to counterstain) after 1 min continuous excitation. For ecells with DTE, after 10 min continuous excitation, the cells were still fluorescing brightly green. Data similar to that shown in FIG. 9 was obtained using DT. However, due to the inability of TRIS buffer to maintain a pH of 8.2 in the DT solutions, this reducing agent was not used in future experiments.

Figure 10:
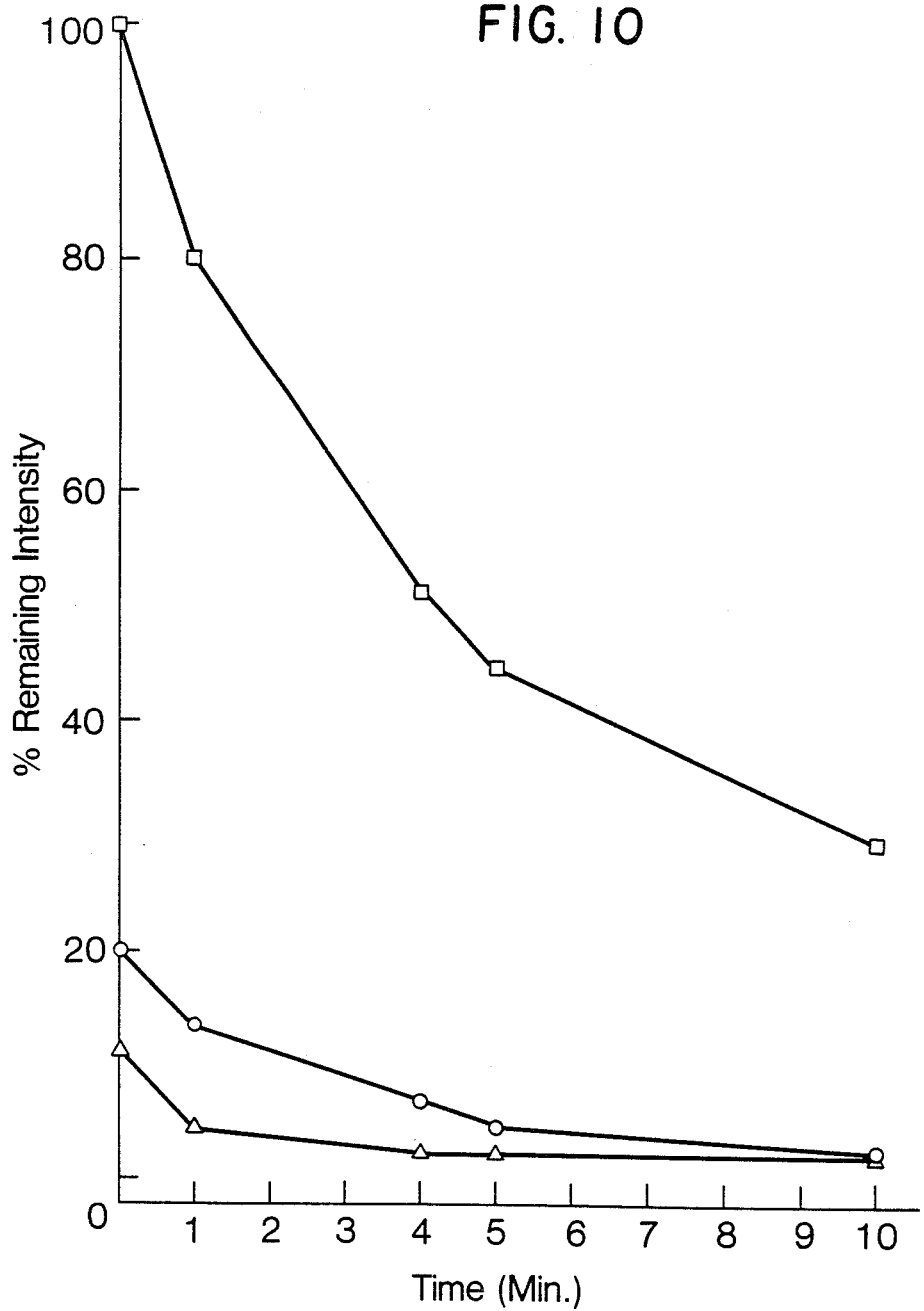
FIG. 10 shows the relationship of the effect of reducing agent on the fading of FITC-labelled ANA cells with rhodamine counterstain during continuous excitation, the % remaining intensity vs the time in min of excitation is plotted. The ANA cells were mounted in buffered glycerol (triangles) and with 0.025M DTE (squares) or 0.3M DABCO (circles).

Verification of the effectiveness of the selected concentrations of the reducing agents on FITC-labeled conjugate to ANA with rhodamine counterstain-treated cells during continuous excitation in the Zonax microfluorophotometer microscope was made. A comparison of percent remaining intensity with 0.025M DTE, 0.3M DABCO and no reducing agent in the buffered glycerol for 10 min continuous excitation is shown in FIG. 10. It should be noted that after 0.1 min, only 20% of the initial fluorescence intensity remains for DABCO. Even after 10 minutes continuous excitation, 20% of the initial intensity remains for DTE as compared to 2.2 and 1.3% for DABCO and buffered glycerol, respectively. However, if DABCO is compared with its own initial intensity as 100%, then, the protection appears to be effective at retaining 25% of its own initial intensity. This indicates that the fading is accelerated by the DABCO initially and then changes at a slower rate and thus imparts stability to the subsequent readings. It may, therefore, be of value as a protector when used for viewing the samples repeatedly. DTE was chosen for subsequent use on the basis of its higher initial fluorescence intensity and greater protective ability over the 10 min measuring period of samples containing DTE, although DTT was almost as effective.

Figure 11:
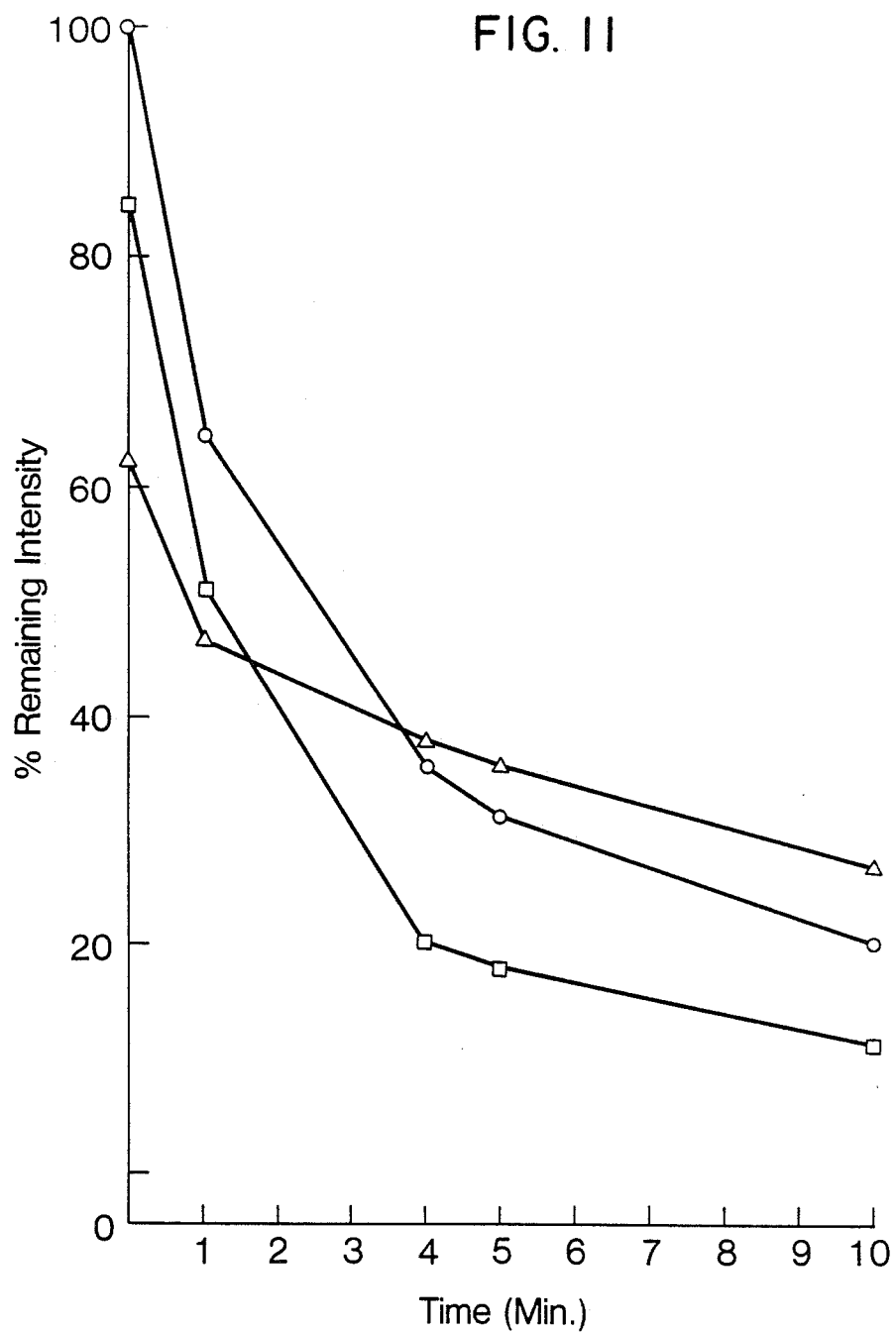
FIG. 11 shows the effects of DTE concentration on fading of FITC-labelled ANA cells with rhodamine counterstain during continuous excitation, the % remaining intensity is plotted vs the time in min of excitation for cells with 0.025M (squares), 0.033M (circles) and 0.05M (triangles) DTE added to the buffered glycerol.

Efforts were made to improve the protective ability of DTE without lowering the initial fluorescence intensity. FIG. 11 shows the fading protection when 0.025, 0.033 or 0.05M DTE was incorporated into the mounting medium for the ANA IF microscopy kit. It should be noted that there is almost a 40% lowering of the initial intensity with 0.05M DTE. Also, 0.05M DTE does not protect the sample better than 0.033M during the first 3.5 min of excitation. Therefore, 0.033M DTE is chosen due to the higher initial fluorescence intensity. The time required to align the specimen in the excitation field is normally less than two minutes, during which 0.033 DTE retains its protective ability.

6. Selection of reducing agent

Based on the above-stated criteria, DTT and DTE were selected as the preferred protecting agents although others could also be used. These reagents offered the most protection from fading with the least inhibition of the initial intensity. It is noted that DABCO at 0.3M lowered the initial intensity 23%.

D. CONCLUSIONS

1. Optimization of chemical environment

The data presented herein indicate that the fading behavior of cell-free conjugates in the fluorometer is a good predictor of the behavior of the fluorophore in the microscope-photometer.

a. Buffer selection

Since the intensity of the fluorescence is dependent on the pH of the medium, it is very important to choose a buffer that can maintain the pH at an optimum value of about 8.2 to 8.5. After testing several buffers, including glycine, TRIS and carbonate, TRIS buffer was found to hold the pH in the optimum range in the presence of reducing agent and also to have the lowest background intensity.

b. Reducing agent selection

The ultimate usefulness of the reducing agents is to inhibit fading while the specimen is being examined microscopically. Therefore, the reducing agents must be able to function with the buffer and pH of the mounting medium. DTE was selected as a preferred reducing agent based upon the selection criteria listed supra. DTE significantly reduced the fading over a 10 min continuous excitation period and did not reduce the initial intensity of the fluorophore. In addition, DTE is easy and practical to use with the buffered glycerol mounting medium. Based on the results in FIG. 8 with DABCO, it is possible that if it were used at a concentration of 0.1M or less, one would encounter only a 10% increase in fading, while the initial intensity would be much higher since higher concentrations of DABCO suppress the fluorescence intensity.

c. Reducing agent concentration

It is necessary to find the lowest concentration of reducing agent that is able to prevent fading for several reasons. First, if the concentration of the agent were too high, reduction of the initial fluorescence may occur and possibly cause faulty end-point determination. Second, the concentration must be low enough so that background intensity is not increased due to autofluorescence of the reducing agent or precipitation of salts on the slide. Table 7 gives the final reducing agent concentration and pH which are preferred in accordance with the present invention for incorporating DTE into buffered glycerol.

TABLE 7

| MOUNTING MEDIUM FOR OPTIMAL PROTECTION | |
|---|---|
| Final Concentration in Buffered Glycerol | |
| TRIS Concentration | 0.05 M |
| DTE concentration | 0.033 M |
| pH | 8.0–8.2 |

2. Kinetics

A more negative slope (%/sec) of the linear regression curve is a measure of fading. Comparing the slopes of the linear regression lines for samples with different reducing agents allows a quick and precise method of comparing the rate of decrease in intensity over a given time period (Table 8). DABCO shows a more negative value and thus indicates greater fading. The other agents show similar slopes and thus are equivalent in protective function when used at their own optimal concentration.

TABLE 8

| SLOPE OF FADING WITH DIFFERENT REDUCING AGENTS | | |
|---|---|---|
| AGENT | conc. M | SLOPE % per sec. |
| DABCO | 0.3 | −17.02 |
| DT | 0.25 | −4.64 |
| DTT | 0.25 | −4.30 |
| DTE | 0.25 | −4.18 |

Figure 12:
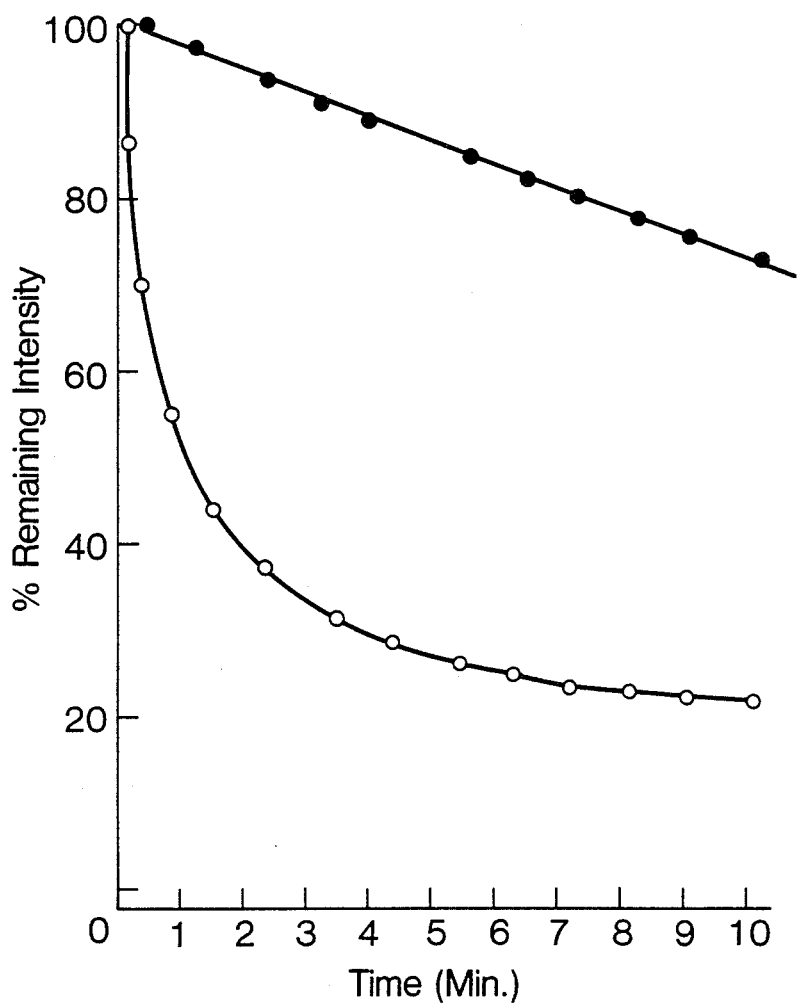
FIG. 12 shows the best fit regression curves for fading of FITC-labelled Rubella cells during continuous excitation when mounted in buffered glycerol (open circles) or 0.05M DTE (solid circles).
Figure 13:
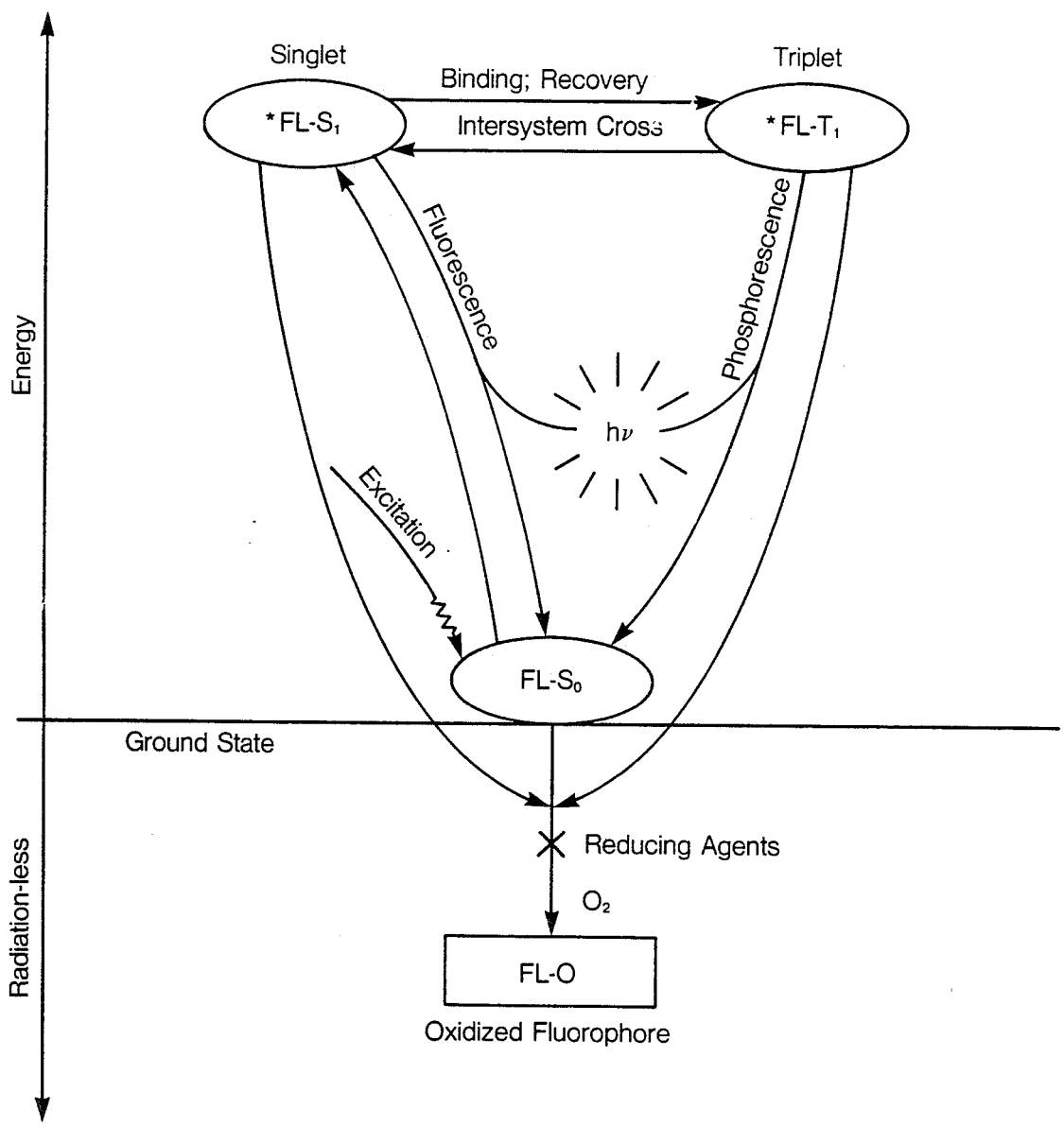
FIG. 13 shows the improvements in fluorescence conversions in accordance with the present invention. Proposed fluorescence conversions showing relative energy levels: Excitation light excites ground state fluorophore (FL-$S_0$) to excited singlet (FL-$S_1$). Light emission occurs with decay to ground state or intersystem crossing to triplet (FL-$T_1$) and then decay to ground state. Radiationless decay by interaction with oxygen to oxidized fluorophore (FL-0) is inhibited in the presence of reducing agents.

FIG. 12 shows the change in fluorescence intensity as a function of excitation time of the labeled Rubella cells mounted in buffered glycerol or with DTE added. When DTT or DTE are present the best fit is a linear regression curve, whereas with no protection, the best fit is a quadratic regression curve. This means that with the reducing agent present, the reaction is of first order, or a function of one rate limiting factor, and without it, the reaction is due to the interaction of two rate limiting factors. This difference may represent two different mechanisms of fading, an oxygen sensitive mechanism and a non-oxygen sensitive mechanism (FIG. 13). Without being bound to any theory, it is hypothesized that the fading in the presence of the reducing agent is non-oxygen sensitive. It should be pointed out, however, that the reducing agents only scavenge the oxygen and that, in no way in the studies described herein, have exhaustive measures been taken to completely remove oxygen from the mounting medium.

Among various utilities of the present invention, those which are of particular significance include:

(1) A kit for use in clinical serology; and (2) Monitoring and quality control of commercially available IF kits;

A kit for quantitative immunofluorescence determination in accordance with the present invention comprises in addition to those components usually or routinely found in a commercial kit of similar type, such as suitable mounting medium, buffer, immunofluorescent reagents and the like, (1) a protective agent which retards fading of fluorescence; (2) a stable fluorophor which allows standardization and calibration of the photometer; (3) counterstains; (4) slides with antigens; (5) fluorescently labelled anti-human antibody; (6) positive and negative controls; (7) instructions to perform the procedure, and the like, in suitable containers if necessary. A kit for quantitative immunofluorescence (QIF) determination as described herein has, of course, not been heretofore available. The prior art kits depend upon visual (subjective) determination. The availability of a QIF kit now makes mechanization, automation and objective commercial as well as clinical applications possible.

As a further illustration of the potential and advantages of the QIF of the present invention, the determination of serum antibodies to two microorganisms, viz., *Toxoplasma gondii* and *Treponema pallidum*, and the estimation of the variability in currently marketed Toxoplasmosis kits using two different lots from three commercially available IF kits are described.

The methods and materials employed in performing these tests are similar to the procedures described herein before, however, the specifics are noted hereunder.

Instrumentation

A Zeiss microscope-photometer is adapted for epifluorescence using an HBO 100 W mercury lamp with a stabilized DC power supply. A microprocessor, Zonax, is integrated with the microscope. A linear interference monochromator is placed in the emission light path to the photomultiplier tube (PMT). The emitted intensity is converted into a voltage reading by the PMT and is displayed on the computer cathode ray tube screen.

The instrument is provided with a series of variable field stops which can mask down the area of the specimen actually illuminated by the exciting light. Adjacent to the PMT, in the emission light path, are also provided diaphragms that can vary the area being measured. The amount of fading during the measurements can be reduced by a fast shutter which excites the specimen for milliseconds.

Software programs provided by Zeiss, control the microscope shutters, field stop, PMT diaphragms, high voltage, amplifier gain and the scanning stage. Either an automatic or a manual measurement protocol could be used.

Experimental

The fluorescence of 67 samples with known titers against *T. gondii* and 42 samples with varying reactivities in the fluorescent Treponema antibody absorbed (FTA-ABS) test were measured. The quantitative system showed a 90% correlation with the visually determined intensity.

Commercial Toxoplasmosis IF Kit

Three individuals read the visual titers and the correlation between the three readers in determining the visual titers of sera positive for *T. gondii* antibodies is shown in Table 9.

TABLE 9

Correlation Between Three Readers in Determining the Visual Titers of FITC-Stained Sera Positive for *T. gondii* antibodies

| Change Titer** | Without DTE English | With DTE English | With DTE Aldrich |
|---|---|---|---|
| −2 | 1 (3%) | 0 | 0 |
| −1 | 8 (21%) | 16 (37%) | 1 (10%) |
| 0 | 15 (39%) | 22 (51%) | 6 (60%) |
| 1 | 13 (34%) | 5 (12%) | 3 (30%) |
| 2 | 1 (3%) | 0 | 0 |
| Total | 38 | 43 | 10 |

*The number of two fold dilutions difference between Kaplan's visually determined titer and that of English or Aldrich.

The presence of DTE in the mounting medium to reduce fading allowed a higher correlation among the readers, producing a smaller spread in the range of the difference in titer as well as a higher percentage of no change in the readings.

For the Toxoplasmosis IF kit, intensities from polar staining and from non-specific fluorescence were eliminated by subtracting as a background the intensity of the dilution of the negative control serum corresponding to the individual specific dilution of the test serum.

Statistical analysis was performed on the data from each of the 67 specimens, from the first dilution to each of the dilutions that one of the readers had visually called the titer. A correlation coefficient, r, describing the linearity of the relationship between log dilution and the photometrically determined intensity was derived. When that relationship (slope of curve) changed from first order to zero order, the end point had been reached. The quantitative titer was then selected as that highest dilution where r=0.94.

Validation of QIF

Figure 14:
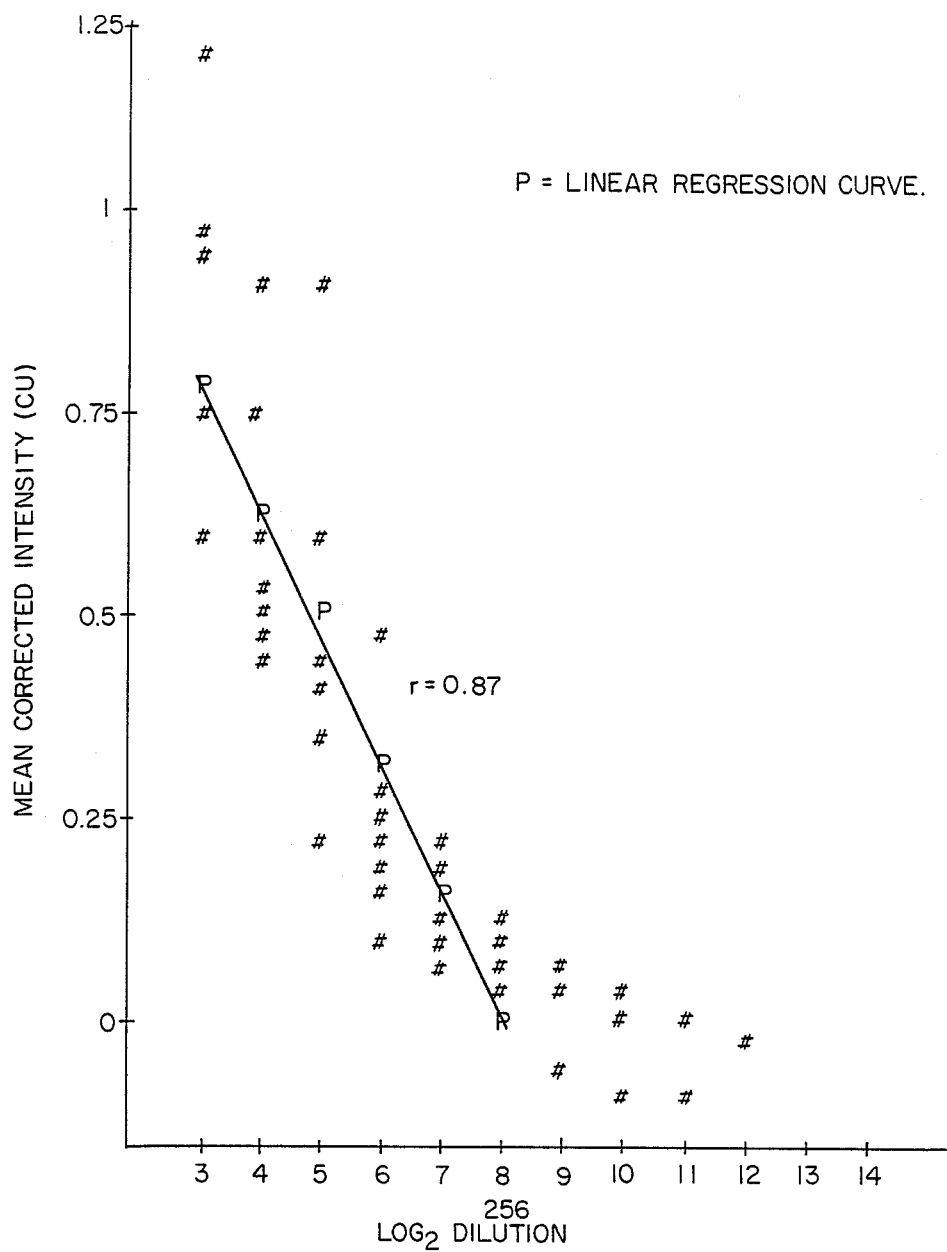
FIG. 14 shows linearity of *Toxoplasma gondii* positive specimens to a 1:256 dilution end point.

All the specimens whose quantitatively determined titer fell at the same dilution were grouped and plotted showing the mean corrected intensity vs $\log_2$ dilution. FIG. 14 is a representative plot showing the 1:256 titer group.

Figure 15:
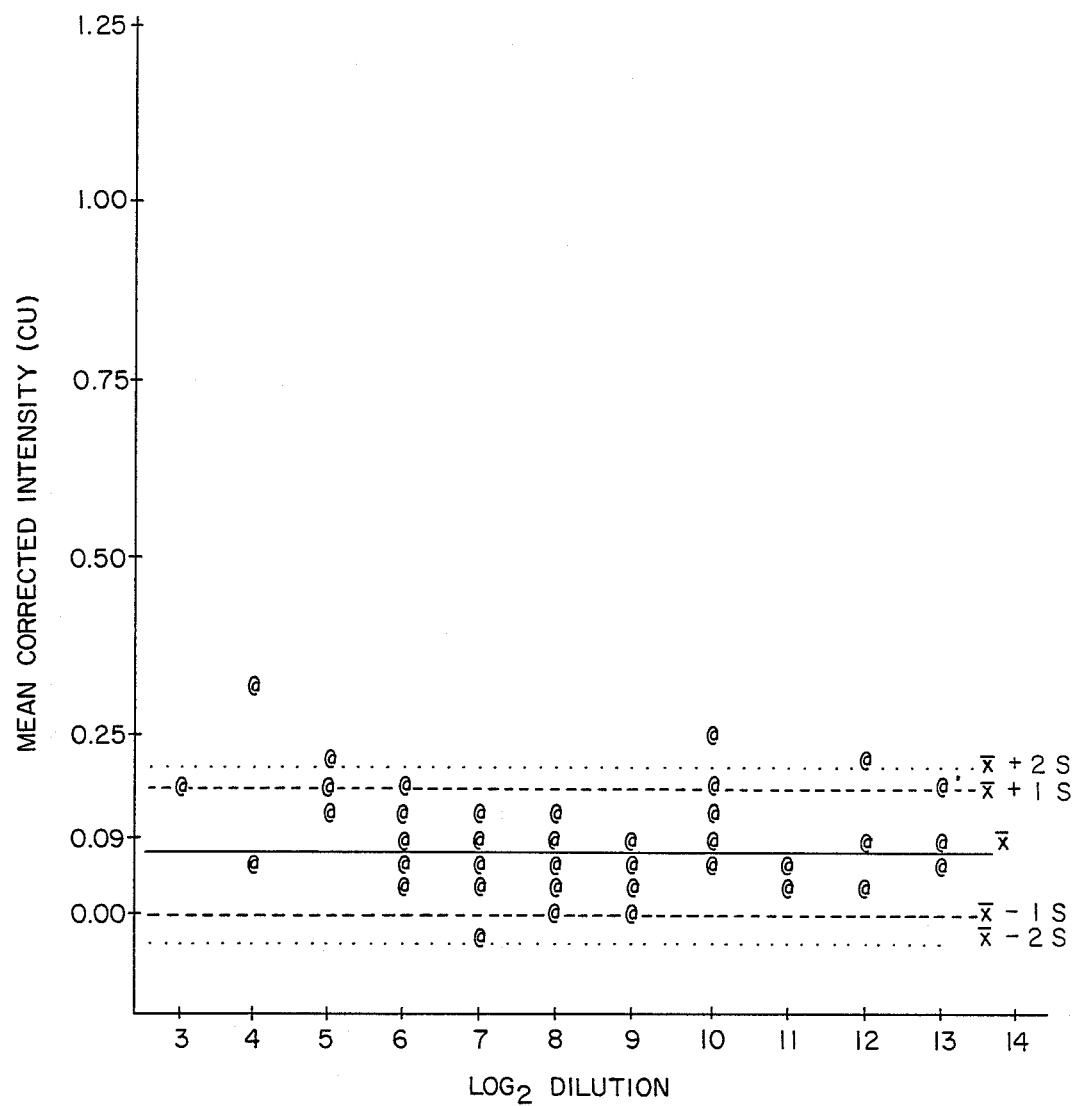
FIG. 15 shows a plot of the mean corrected intensity at the titer dilution of 67 sera positive for *T. gondii* antibodies vs quantitative titer.

Using two different manufacturer's IF kits, the intensities at the titer were found to be similar (FIG. 15) with a mean intensity of 0.09 and a range from −0.05 to 0.22. This range is caused by the varying concentrations of antibodies in each sera, as well as the proportion of each class of antibody and other factors such as albumin and blocking factors in the serum.

The fluorescence of sera (at a 1:16 dilution) from patients known to have a titer less dilute than 1:8 and, therefore, considered negative for antibodies to *T. gondii*, was measured to compare the intensity of positive sera (at the titer dilution) to the negative sera (Table 10).

TABLE 10

Summarization of Mean Corrected Intensities for FITC-Labeled *Toxoplasma gondii* Cells Toxoplasmosis IF Kit

| | No. | Mean ± SD (Corning Units) |
|---|---|---|
| Positive clinical specimens at titer dilution | 67 | 0.09 ± 0.07 |
| Positive controls at 1:128 dilution | 6 | 0.58 ± 0.24 |
| Negative clinical specimens at 1:16 dilution | 49 | 0.05 ± 0.02 |

This intensity (mean=0.05) represents a baseline, non-specific intensity due to any cause and is a component of all dilutions of the sample.

Since the mean of positive specimens at the end point is 0.09 and the mean of the negative specimens is 0.05, a cut-off intensity level of 0.09 which is approximately two times that of the mean of the negative sera, was established as an optimum end point.

Use of QIF

Using control materials with the QIF technique, variability in the intensities of 2 different lots from 3 commercially available Toxoplasmosis IF kits (Table 11), was determined.

TABLE 15

Analysis of Variance of Commercial Toxoplasmosis IF Kits Using 1:128 Dilution of a High Positive Control Serum

| Manufacturer | Variance Source | Mean* Intensity | Variance Component | Percent |
|---|---|---|---|---|
| | Lot | | 0.166 | 87.62 |
| | 8166 | 0.267 | | |
| | 8805 | 0.843 | | |
| A | Slide | | −0.001 | 0.0 |
| | Well | | 0.004 | 2.16 |
| | Error | | 0.019 | 10.22 |
| | Lot | | 0.001 | 10.56 |
| | 030 | 0.495 | | |
| | 038 | 0.448 | | |
| B | Slide | | 0.0 | 0.0 |
| | Well | | 0.001 | 13.18 |
| | Error | | 0.007 | 76.26 |
| | Lot | | 0.128 | 88.99 |
| | 013 | 0.852 | | |
| | 014 | 0.346 | | |
| C | Slide | | 0.0004 | 0.31 |
| | Well | | 0.003 | 1.91 |
| | Error | | 0.013 | 8.78 |

*Four slides were prepared from each lot and ten cells on each of 3 well were measured.

This analysis showed that for 2 manufacturers there was a 50% difference between the intensities from their own lots when tested with the control sera. The other differences between wells, slides and replications were not greater than that among individual cells. This indicates that for one manufacturer at least, the variability as a result of producing the kits is as good as required, since it is less than the biological variability among the cells. It further indicates that if the QIF technique were used by the manufacturer to quality control the production lots, the quantitative measure could be used to adjust the intensity values closer to each other for each lot. This would result in less confusion for the user since the user would not encounter large differences in intensities from lot to lot or manufacturer to manufacturer.

FTA-ABS IF Kit

Validation of QIF

Figure 16:
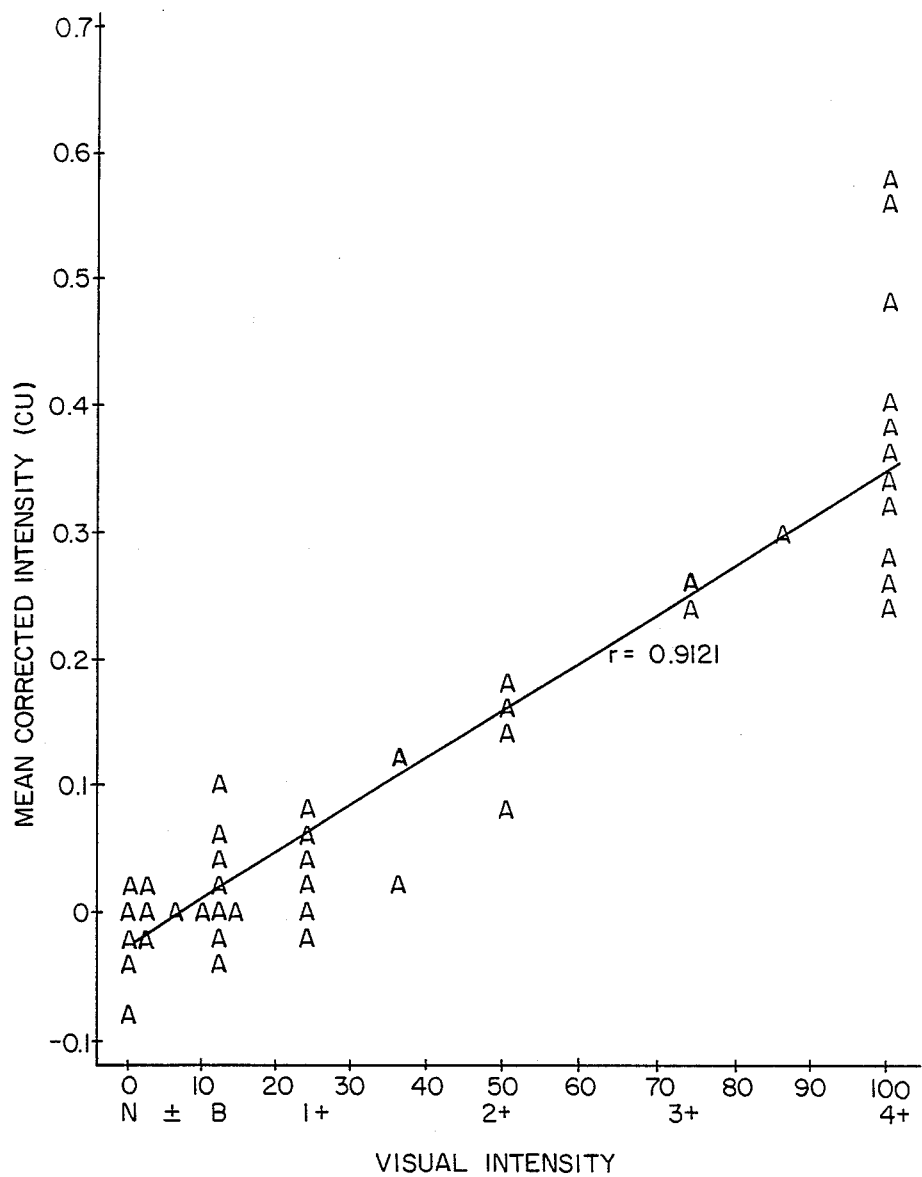
FIG. 16 shows correlation of mean corrected intensity with visual intensity on 42 specimens for the FTA-ABS test.

FIG. 16 shows a plot of the mean corrected intensity (after subtracting the intensity of the non-specific serum diluted in sorbent as a background) vs the visual intensity for labeled Treponema cells.

The 0.9121 correlation coefficient showed that the visual intensity is proportional to the quantitative intensity from the B up to the 4+ intensity. The 4+ intensities above 0.4 Corning Units may represent saturation.

The intensities were grouped into three ranges based upon the correlation to the photometrically-determined intensity values with the subjective, visual readings which are currently used in the serological diagnosis of antibodies to *T. pallidum.* (Table 12).

TABLE 12

Summarization of Mean Corrected Intensities for FITC-Labeled *Treponema pallidum* Cells FTA-ABS IF Kit

| Group | Clinical Designation | Quantitative Intensity Range | No. | Visual Reading |
|---|---|---|---|---|
| 1 | Negative | −0.07 to 0.015 | 15 | N/±/B |
| 2 | Borderline | 0.02 to 0.07 | 9 | B/1+ |
| 3 | Positive | 0.08 to 0.16 | 18 | 2+ |
|   |   | 0.24 to 0.30 |   | 3+ |
|   |   | 0.33 to 0.58 |   | 4+ |

Table 13 summarizes the validation of the visual and the QIF methods using clinical specimens.

TABLE 13

Validation with Clinical Specimens

|   | No. | r |
|---|---|---|
| Toxoplasmosis IF kit | | |
| Log$_2$ dilution vs corrected intensity | 67 | 0.85 |
| Visual vs QIF method | 67 (61)* | 0.79 (0.85) |
| Positive and Negative specimens | 116 (110) | 0.88 (0.92) |
| FTA-ABS IF kit | | |
| Visual vs QIF method | 42 | 0.91 |

*Numbers in parenthesis refer to data from English.

Since a 90% or better correlation with the visual method of determining titers can be obtained with the QIF technique of the present invention, this technique can replace the subjective, visual method of end point determination. As mentioned before, this technique, therefore, permits daily and inter-laboratory comparisons of intensity values compensating for lamp aging or variation in excitation energy. The addition of chemical additives to the mounting medium reduces fading, thereby stabilizing the intensity values.

The method of the present invention also eliminates retesting the sera due to the variability and uncertainty associated with visually determined titers. The occurence of false-positive and false-negative reactions also decreases. The diagnostic significance of the QIF procedure also improves significantly due to an accurate, reproducible method for monitoring the fluorescent reaction product.

Use of these types of measurements also enables the establishment of guidelines for regulatory purposes. The QIF allows the establishment of a measurement protocol with objective criteria.

The ability to scan without fading also permits the introduction of automated or semi-automated instrumentation to determine the end point quantitatively.

Procedural parameters for Toxoplasmosis and Treponema are now summarized.

I. Measurement of immunofluorescent Toxoplasma gondii

A. Measuring parameters
 1. 63×/1.4 Phase 3 oil objective
 2. Wide band FITC filter set (set #3), 450–490 nm excitation/LP520 emission.
 3. PMT diaphragm=0.63 (red).
 4. Field stop=0.63
 5. D=1, fluorescence mode.
 6. Monochromator="White light" position and KP-560 emission filter inserted into emission light path.
 7. Fluorescence free (FF) oil (Cargille).

B. Localization of cells
 1. Turn off epi-illumination "F1" and turn on transmitted light "F2".
 2. Focus on cells under phase contrast optics (using phase 3 condenser ring).
 3. Slide the prism slider (located on the top right of microscope under PMT diaphragms) to middle (orange) position.
 4. At this point a circular measuring diaphragm in the center of the field will be seen. Using the 4 arrow keys on the keyboard, align a single (normal appearance) cell under the measuring aperture.

C. Measurement of cells
 1. Once the cell is aligned, the high voltage (HV) is adjusted to approximately 675 and the gain to 100 and an instantaneous intensity reading is taken. The intensity is preferred to be approximately 70–90 intensity units. This prevents saturation of the PMT due to variability in intensities of cells. If the intensity is not in this range, the HV is adjusted to make the intensity fall in the preferred range.
 2. Clear the channel "C". Make sure to be back in transmitted illumination. (After pressing "return", the program automatically shuts off the epi-light and turns on transmitted light).
 3. Locate a new cell in a previously unexposed field. Take an instantaneous intensity reading. If titering a patient sera, measure a total of 3 cells per dilution well (locating each under phase contrast and taking an instantaneous reading).
 4. Measure the negative control under the same HV, gain and instrument settings as the positive cells were measured.

II. Measurement of immunofluorescent Treponema pallidum in FTA-ABS Test

A. Localization of Samples. The cells were located under darkfield, in order not to fade the specimen before quantitative measurements. For darkfield microscopy, an Apo 40×/1.00 Ph. 3 oil objective with an adjustable iris diagphragm, wich adjusts to a NA of 0.6, was used with a 1.2/1.4 oil darkfield condensor. The iris diaphragm was closed down to the 0.6 aperture for localization of the cells under darkfield, but was opened to 1.0 for quantitative fluorescence measurements.

B. Alignment of cells under measuring aperture. The cells were aligned under the 0.63 mm PMT measuring diaphragm (using a 0.63 mm diameter field stop, the area sensed was approximately 32 $\mu m^2$). The cells did not always fit completely inside the measuring aperture, but the same sensing area was always measured.

C. Measurement of cells.

1. Reading standards. The following standards are used. (1) 4+reactive control, (2) 1+reactive control and (3) Non-specific control diluted in sorbent. Ten cells were measured for each standard by taking an instantaneous intensity reading.

2. Positve specimens. Ten cells were measured in each well (without the KP-560 filter) by taking instantaneous readings.

3. Data analysis. The intensities were corrected based on the linear regression parameters of the standard calibration curve. The mean intensity for the 10 cells reacted with the non-specific serum control diluted in sorbent was subtracted from the intensity of each of the cells reacted with sera positive for *T. pallidum* antibodies. For each patient serum, the intensity of the 10 cells was averaged. An arbitrary scale was developed to relate the visually determined results to a linear scale from 0 to 100. The mean corrected intensity vs the visual intensity in arbitrary units was plotted.

It is understood that the examples and embodiments described herein are for illustrative purposes only and that various modifications or changes in light thereof will be suggested to persons skilled in the art and are to be included within the spirit and purview of this application and the scope of the appended claims.

We claim:

1. A method for quantitative determination of *Toxoplasma gondii* antibody titer in a biological sample by immunofluorescent photometric microscopy, comprising: (a) reacting a specimen of said sample with an immunofluorescent reagent in a mounting containing a protective agent in an amount sufficient to reduce fading of a fluorescent reaction product less than 25% of initial fluorescent intensity; (b) localizing the specimen under transmitted, visible light; (c) reducing the effect of counterstain intensity by filters in emission light path; (d) measuring the sample using a fast shutter; (e) calibrating the photometer used in said microscopy by a stable fluorophore; (f) recording intensity of fluorescence of said specimen compared to standard negative and positive controls (g) reducing effect of polar staining by subtracting the corrected intensity of corresponding dilution of the negative control from the sample reading; and (h) assigning a numerical endpoint for serum antibody levels against Toxoplasma gondii.

2. A method for quantitative determination of *Treponema pallidum* antibody titer in a biological sample by immunofluorescent photometric microscopy, comprising (a) reacting in a mounting medium containing a protective agent in an amount sufficient to reduce fading of fluorescent reaction product less than 25% of initial fluorescent intensity; (b) improving signal to noise ratio by minimizing area of microscope slide from which light intensity is measured, or by stabilizing direct current power supply to excitation lamp of photometer; (c) localizing the specimen under transmitted, visible light; (d) measuring the sample using a fast shutter; (e) calibrating the photometer used in said microscopy by a stable fluorphore; (f) recording intensity of fluorescence of said specimen relative to an established corrected intensity for cut off range between standard positive and negative controls; and (g) assigning a numerical endpoint for determination of antibody levels against Treponema pallidum.

3. The method of claim 1 wherein the stable fluorophore is incorporated into the immunofluorescent reagent.

4. The method of claim 1 wherein said protective agent is selected from the group consisting of sodium dithionite, dithioerythritol, dithiothreitol and triethylene-diamine.

5. The method of claim 4 wherein said protective agent is dithioerythritol.

* * * * *